US011836810B2

(12) United States Patent
Cunningham et al.

(10) Patent No.: US 11,836,810 B2
(45) Date of Patent: Dec. 5, 2023

(54) SYSTEM AND METHOD FOR USER INTERFACE AND DATA PROCESSING MANAGEMENT FOR CLINICAL TRIAL ADMINISTRATION SYSTEMS

(71) Applicant: GREENPHIRE, LLC, King of Prussia, PA (US)

(72) Inventors: Kyle Russell Cunningham, Schwenksville, PA (US); Zachary Andrew Hales, Trappe, PA (US)

(73) Assignee: GREENPHIRE, LLC, King of Prussia, PA (US)

( * ) Notice: Subject to any disclaimer, the term of this patent is extended or adjusted under 35 U.S.C. 154(b) by 0 days.

(21) Appl. No.: 16/429,227

(22) Filed: Jun. 3, 2019

(65) Prior Publication Data

US 2019/0370907 A1    Dec. 5, 2019

Related U.S. Application Data

(60) Provisional application No. 62/679,462, filed on Jun. 1, 2018.

(51) Int. Cl.
*G06Q 40/12* (2023.01)
*G16H 10/20* (2018.01)
*G06F 9/451* (2018.01)

(52) U.S. Cl.
CPC ........... *G06Q 40/123* (2013.12); *G06F 9/451* (2018.02); *G16H 10/20* (2018.01)

(58) Field of Classification Search
None
See application file for complete search history.

(56) References Cited

U.S. PATENT DOCUMENTS 8,000,983 B2    8/2011 Alves
8,099,342 B1 *  1/2012 Christian ............. G06Q 40/123
                                                   705/31

(Continued)

FOREIGN PATENT DOCUMENTS

WO    2011103523    8/2011

OTHER PUBLICATIONS

Darmouth "Guidance Concerning Payments to Research Participants," Guarini School of Graduates and Advanced Studies, Jun. 18, 2014. Retrieved on Jul. 29, 2019, Retrieved from: <URL:https://graduate.dartmouth.edu/guidance-concerning-payments-research-participants> entire document.

(Continued)

*Primary Examiner* — Peter Ludwig
(74) *Attorney, Agent, or Firm* — FISHERBROYLES, LLP

(57) ABSTRACT

A clinical data processing system comprising a processor; a memory operatively coupled to the processor, the memory storing executable instructions providing a user interface module configured to receive participant data and store it as participant data in the memory; a schema management module configured to receive input via the user interface module, the schema management module comprising rules for determining withholding amounts for payments due to a participant in view of applicable schema data and participant data stored in the memory; and a participation aggregation module configured to receive input via the user interface module, the participation aggregation module comprising rules for determining whether to permit or defer payments due to the participant in view of aggregated payments due to a participant as reflected in participant data stored in the memory.

17 Claims, 19 Drawing Sheets

(56) References Cited

U.S. PATENT DOCUMENTS

| | | | | |
|---|---|---|---|---|
| 8,204,805 | B2* | 6/2012 | Eftekhari | G06Q 40/02 705/31 |
| 8,719,049 | B2* | 5/2014 | Samar | G06Q 10/10 705/2 |
| 10,664,925 | B2* | 5/2020 | Wang | G06Q 40/123 |
| 10,664,926 | B2* | 5/2020 | Wang | G06F 40/205 |
| 2001/0044734 | A1* | 11/2001 | Walker | G06Q 40/08 705/4 |
| 2003/0208378 | A1* | 11/2003 | Thangaraj | G16H 30/40 705/2 |
| 2003/0216978 | A1* | 11/2003 | Sweeney | G06Q 40/12 705/30 |
| 2004/0078271 | A1* | 4/2004 | Morano | G06Q 40/02 705/19 |
| 2004/0254927 | A1* | 12/2004 | Lang | G06Q 40/02 |
| 2005/0010451 | A1* | 1/2005 | Marks | G16H 10/20 705/3 |
| 2005/0182664 | A1 | 8/2005 | Abraham-Fuchs | |
| 2006/0016468 | A1 | 1/2006 | Zheng | |
| 2006/0161468 | A1 | 7/2006 | Larsen | |
| 2007/0094104 | A1 | 4/2007 | Reahard | |
| 2007/0255587 | A1 | 11/2007 | Chien | |
| 2008/0010178 | A1* | 1/2008 | Savard | G06Q 40/123 705/31 |
| 2008/0027783 | A1 | 1/2008 | Hughes | |
| 2008/0270181 | A1* | 10/2008 | Rosenberg | G06Q 10/06393 705/2 |
| 2008/0288285 | A1 | 11/2008 | Mancini | |
| 2009/0012884 | A1* | 1/2009 | Harman | G06Q 10/10 705/31 |
| 2009/0037305 | A1* | 2/2009 | Sander | G06Q 40/123 705/31 |
| 2009/0112662 | A1 | 4/2009 | Mullen | |
| 2010/0116882 | A9 | 5/2010 | Harrison | |
| 2010/0138235 | A1* | 6/2010 | Marks | G16H 40/67 705/2 |
| 2010/0228699 | A1* | 9/2010 | Webber | G06F 21/6245 707/622 |
| 2011/0202370 | A1 | 8/2011 | Green, III | |
| 2011/0265112 | A1 | 10/2011 | Kwak | |
| 2012/0004926 | A1* | 1/2012 | Samar | G06Q 10/10 705/2 |
| 2012/0004927 | A1* | 1/2012 | Marks | G16H 40/67 705/2 |
| 2012/0072321 | A1* | 3/2012 | Christian | G06Q 40/123 705/31 |
| 2012/0109792 | A1* | 5/2012 | Eftekhari | G06Q 40/02 705/31 |
| 2012/0153419 | A1 | 6/2012 | Itonaga | |
| 2013/0080186 | A1* | 3/2013 | Marks | G16H 40/67 705/2 |
| 2013/0275279 | A1* | 10/2013 | Raymond | G06Q 40/10 705/30 |
| 2013/0282608 | A1* | 10/2013 | Raymond | G06Q 10/1057 705/322 |
| 2013/0290200 | A1* | 10/2013 | Singhal | G06Q 10/0637 705/317 |
| 2014/0236619 | A1* | 8/2014 | Samar | G06Q 10/10 705/2 |
| 2014/0244457 | A1* | 8/2014 | Howell | G06Q 40/02 705/31 |
| 2015/0242834 | A1 | 8/2015 | Goldsmith | |
| 2015/0286802 | A1* | 10/2015 | Kansara | G16H 10/20 705/3 |
| 2016/0140668 | A1* | 5/2016 | Maguire | G06Q 40/123 705/31 |
| 2016/0188845 | A1 | 6/2016 | Harder | |
| 2016/0246936 | A1 | 8/2016 | Kahn | |
| 2016/0247239 | A1* | 8/2016 | Houseworth | G06Q 40/123 |
| 2017/0004583 | A1* | 1/2017 | Wang | G06Q 40/123 |
| 2017/0004584 | A1* | 1/2017 | Wang | G06Q 40/123 |
| 2017/0186099 | A1* | 6/2017 | Lubczynski | G06Q 40/123 |
| 2018/0033092 | A1* | 2/2018 | Wang | G06Q 40/123 |
| 2018/0114274 | A1* | 4/2018 | Wang | G06F 40/56 |
| 2018/0114275 | A1* | 4/2018 | Wang | G06Q 40/123 |
| 2018/0150913 | A1* | 5/2018 | Wang | G06Q 40/123 |
| 2019/0370907 | A1 | 12/2019 | Cunningham | |
| 2020/0143912 | A1* | 5/2020 | Rosenberg | G06Q 10/06393 |
| 2020/0193527 | A1* | 6/2020 | Hanekamp, Jr. | G06Q 40/123 |

OTHER PUBLICATIONS

International Search Report dated Aug. 9, 2019 for International Application No. PCT/US2019/035070.
Written Opinion of the International Searching Authority dated Aug. 9, 2019 for International Application No. PCT/US2019/035070.
Extended European Search Report dated Jan. 12, 2022, in European Application No. 19812335.8.
International Search Report and Written Opinion of the International Searching Authority dated Aug. 2, 2021, in International Application No. PCT/US21/29681.
"Siebel Clinical Trial Management System Guide", by Siebel Information Development Team, takemn from https://docs.oracle.com/cd/ 95904_01/books/CTMS/setting-up-and-making-clinical-payments. html#c_Reversing_Splits_for_Payment_Activities_am1022787 18 pages (Year: 2018).
"Siebel Clinical Trial Management System Guide", by Siebel Information Development Team, taken from https://docs.oracle.com/cd/ F26413_31/books/CTMS/c-Setting-Up-Clinical-Regions--ab1048246. html#ab1048246,3 pages (Year: 2018).
Micrsoft® Excel 2010 for Dummies, by Greg Harvey, published Apr. 26, 2010, taken from https://www.landlordleaseforms.com/ forms/ landlord-ebooks/microsoft-office-excel-2010-for-dummies. pdf, pp. C, ci, 1, 2, 62, 63 (Year: 2010).
How to create Progress bar using conditional formatting in Excel 2013, 2010, and 2007, taken from https://tipsmake.com/ how-to-create-progress-bar-using-conditional-formatting-in-excel-2013-2010-and-2007,published May 25, 2019, by Samuel Daniel, 8 pages (Year: 2019).

* cited by examiner

ClinCard

WELCOME, CLINCARD USER
User Settings | Support | Logout

REGISTER SUBJECT | LOOK UP SUBJECT | PAYMENT APPROVALS | TRAVEL APPROVALS | ADMIN | REPORTS

Taxes have been withheld from this payment. To prevent taxes from being withheld on future payments, the study participant must provide their Tax Identification Number (TIN).

Look Up Subject

< Return to Search Results

JANE H. DOE

SUBJECT INFORMATION | AUDIT HISTORY

Study Name
XYZ Study 1

Subject I.D.
1216-1019

Card Balance
0.00 USD

Pending Payments
0.00 USD

YTD Earnings
550.00 USD

Card Number
XXXX-XXXX-XXXX-9059

Expiration Date
03/31/2017

Study Status
Enrolled

Address
345 Any Street
Garden Plaza
Anytown, Delaware 12345

Timezone
America/Chicago

Allow Email
No

Recent Activity
Created new subject John Doe
Removed $100.00 from card X-5209 per client request.
Note: Void requested by John Doe
Voided payment of $100.00 for Jane Doe
Created new subject John Doe
VIEW ALL ASSIGN CLINCARD
REQUEST PAYMENT
REQUEST REIMBURSEMENT
CREATE TRAVEL PROFILE
EDIT SUBJECT INFORMATION
SCHEDULE APPOINTMENT Upcoming Appointments   Time zone: America/Chicago

| DATE | DAY | TIME | STUDY | SCHEDULER |
|------|-----|------|-------|-----------|

Fig. 7

SYSTEM AND METHOD FOR USER INTERFACE AND DATA PROCESSING MANAGEMENT FOR CLINICAL TRIAL ADMINISTRATION SYSTEMS

CROSS-REFERENCE TO RELATED APPLICATION

This application claims the benefit of priority, under 35 U.S.C. § 119(e), of U.S. Provisional Patent Application No. 62/679,462, filed Jun. 1, 2018, the entire disclosure of which is hereby incorporated herein by reference.

FIELD OF THE INVENTION

The present invention relates generally to computerized information processing systems, and more particularly to a system and method for user interface and data processing management for clinical trial administration systems. The disclosed technology may be applied, for example, to perform data processing required for managing withholding obligations for payments to participants of clinical trial studies.

BACKGROUND

In the field of computerized devices and computer-implemented data processing systems and user interfaces, there are many technical challenges facing the designer of such interfaces. These technical challenges are discussed below.

By way of industry background, pharmaceutical, medical device and biotechnology (sponsor) companies that wish to bring a product to market in the United States must have their product undergo Food and Drug Administration (FDA) reviewed clinical studies. The purpose of these studies includes testing the efficacy and safety of products on human subjects (also, referred to herein as patients or Study Participants).

Clinical studies often provide compensation to Study Participants for their time, effort and expenses incurred. Typically, this is an expense borne by the sponsor of the study and administered by the study coordinators or "investigators" who interact with the subjects in a trial, and must adhere to the study-specific protocols that govern the study and that detail the structure of patient compensation. Historically, these payments were made via cash or check. However, recent advances in clinical payment technology allows payments to be transfer of funds to be provided in a real-time manner via a prepaid debit card or directly into a banking account, thereby providing the same access to compensation as historic payment methods, while establishing central electronic based records detailing the time, amount, and parties involved in a compensation transaction. One system for automating clinical payments to Study Participants is described in U.S. Pat. No. 8,719,049 to Samar et al., issued May 6, 2014 and entitled "Automated method of reporting payments made to patients for their participation in a clinical study in a blinded manner to the sponsor of the clinical study," the entirety of which is incorporated herein by reference.

Payments for participation in the clinical studies may be subject to various tax withholding laws or other schema. For example, in the United States, the Internal Revenue Service (IRS) currently requires that anyone participating in a clinical trial who receives more than $600 per year from a clinical research site must receive a 1099-MISC form. The rules for applying withholding, etc. can vary according to the location or citizenship or participants, etc., and can be complex, especially if an individual participates in multiple clinical studies.

Accordingly, in the context of clinical trial administration, technical challenges occur in the form of a need for a data processing system that is capable of tracking disparate tax or other schema (such as withholding requirements), user/operator specific preferences as to how such withholding requirements will be addressed, which may account for varied interpretations of such withholding requirements, and applying them appropriately for payment management purposes. Current data processing systems typically track withholding requirements uniformly, according to a single withholding schema (e.g., a US/federal withholding schema), and typically apply such requirements uniformly, across all payees, and are incapable of applying different withholding schema (e.g., US/federal, German, Japanese, etc.) to different payees, or to addressing varied interpretations of a single set of withholding requirements according to user/operator preferences.

Further, for example, under the U.S. federal taxation schema, the $600 threshold applies to the total received by the Study Participant over a year. Thus, if the Study Participant is compensated for multiple studies that are under $600 individually, but together add up to the IRS' $600 threshold, the Study Participant must receive a 1099 form; however, if the participant does not reach the threshold, the form is not required.

Further technical challenges occur in the form of a need for processing data in a more sophisticated fashion that allows for tracking of activities and payments in an aggregated fashion, so that withholding obligations may be tracked more broadly in support of per-participant taxation obligations. Current data processing systems typically track payments solely on a per-study basis, and are incapable of capturing data across multiple studies. This leads to erroneous data processing that provides an inaccurate representation of the participant's aggregate income, and thus produces inaccurate withholding data.

Further still, these technical challenges occur in the form of a need for a simple user interface that allows an unsophisticated user to engage with the user interface in straightforward fashion to apply complex and varied withholding requirements across multiple payees, and to track withholding requirements for a single payee across multiple studies.

Accordingly, although data processing systems for administration of clinical trials have made it easier to provide compensation to Study Participants, conventional data processing systems lack the ability to manage withholding that addresses the complexities of payments for clinical studies. Thus, it is desired to integrate functionality into such data processing systems that provides withholding management capabilities in the context of clinical studies.

SUMMARY

Embodiments of the present invention address and overcome one or more of the above shortcomings and drawbacks, by providing methods, systems, and apparatuses related to data processing in support of clinical trial administration.

According to one aspect, the present invention provides a clinical data processing system comprising: a processor; a memory operatively coupled to the processor, the memory storing executable instructions providing: a user interface module configured to receive participant data and store it as participant data in the memory; a schema management module configured to receive input via the user interface module, the schema management module comprising rules for determining withholding amounts for payments due to a participant in view of applicable schema data and participant data stored in the memory; and a participation aggregation module configured to receive input via the user interface module, the participation aggregation module comprising rules for determining whether to permit or defer payments due to the participant in view of aggregated payments due to a participant as reflected in participant data stored in the memory Optionally, the clinical data processing system may further include executable instructions stored in the memory to provide a validation engine configured to identify a Taxpayer Identification Number (TIN) and to communication via a communications network to a remote server to validate the TIN.

The present invention provides a system for receiving personal information corresponding to a Study Participant, receiving tax management settings comprising a withholding option specifying how withholding should be applied to clinical payments to the Study Participant, receiving one or more requests for payment to the Study Participant for participation in one or more clinical studies, wherein each request comprises a payment amount and a description of a corresponding activity related to a clinical study; and processing each request for payment by: (i) determining a withholding amount to be applied to the payment amount of the request based on the tax management settings; and (ii) determining an amount of payment due to the Study Participant by subtracting the withholding amount from the requested payment amount.

Further still, the present invention provides a Clinical Data Processing System capable of being configured according to user/operator preferences, e.g., to perform data processing in a manner consistent with the user/operator's preferences, e.g., in view of a user/operator-specific interpretation of governing tax laws as to how to apply withholding rules according to each user/operator's preferences and/or interpretation of the governing tax laws—e.g., to apply withholding to all payments, only to payments that make total payments exceed a predetermined threshold, or only to portions of payments that make total payments exceed a predetermined threshold. Additionally, TIN validation may be provided, and withholding may be applied selectively according to whether a valid TIN has bene provided to the system.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there are shown in the drawings embodiments that are presently preferred, it being understood, however, that the invention is not limited to the specific instrumentalities disclosed. Included in the drawings are the following Figures:

FIGS. 5A-5K provide example graphical user interfaces (GUIs) for performing tax management of clinical study payments, according to some embodiments;

DETAILED DESCRIPTION

The present invention relates to computerized systems and methods for administering clinical trials, particularly payment-related data processing in support of clinical trials, and for creation of user interfaces displayable on computerized computing devices. More specifically, the present invention provides a system and method for user interface and data processing management for clinical trial administration systems. In particular, the present invention provides a Clinical Data Processing System providing an improvement in the functioning of the computer system and the technology used in the associate technical field in that the present invention provides a system and method capable of processing data in a novel and more sophisticated fashion that allows for tracking of activities and payments for a single participant in an aggregated fashion that accounts for participant payments across multiple clinical trial studies, so that withholding obligations may be met with accuracy, thereby improving the associated technology and providing an improvement to state-of-the art computer systems. Further, the present invention provides a Clinical Data Processing System capable of tracking disparate schema (e.g., taxation, withholding, or otherwise) applicable to participants in multiple domestic and foreign jurisdictions, and performing data processing in accordance with such varied schema. Further still, the present invention provides a Clinical Data Processing System capable of being configured according to user/operator preferences, e.g., to perform data processing in a manner consistent with the user/operator's preferences, e.g., in view of a user/operator-specific interpretation of governing tax laws. Further still, the present invention provides a Clinical Data Processing System that provides a straightforward user interface enabling an unsophisticated user to easily configure, in a simple-to-understand fashion, the Clinical Data Processing System to perform accurate data processing for multiple participants in varied jurisdictions, in which varied withholding schema apply, while aggregating data from each participant's involvement across multiple clinical trial studies.

Figure 1:
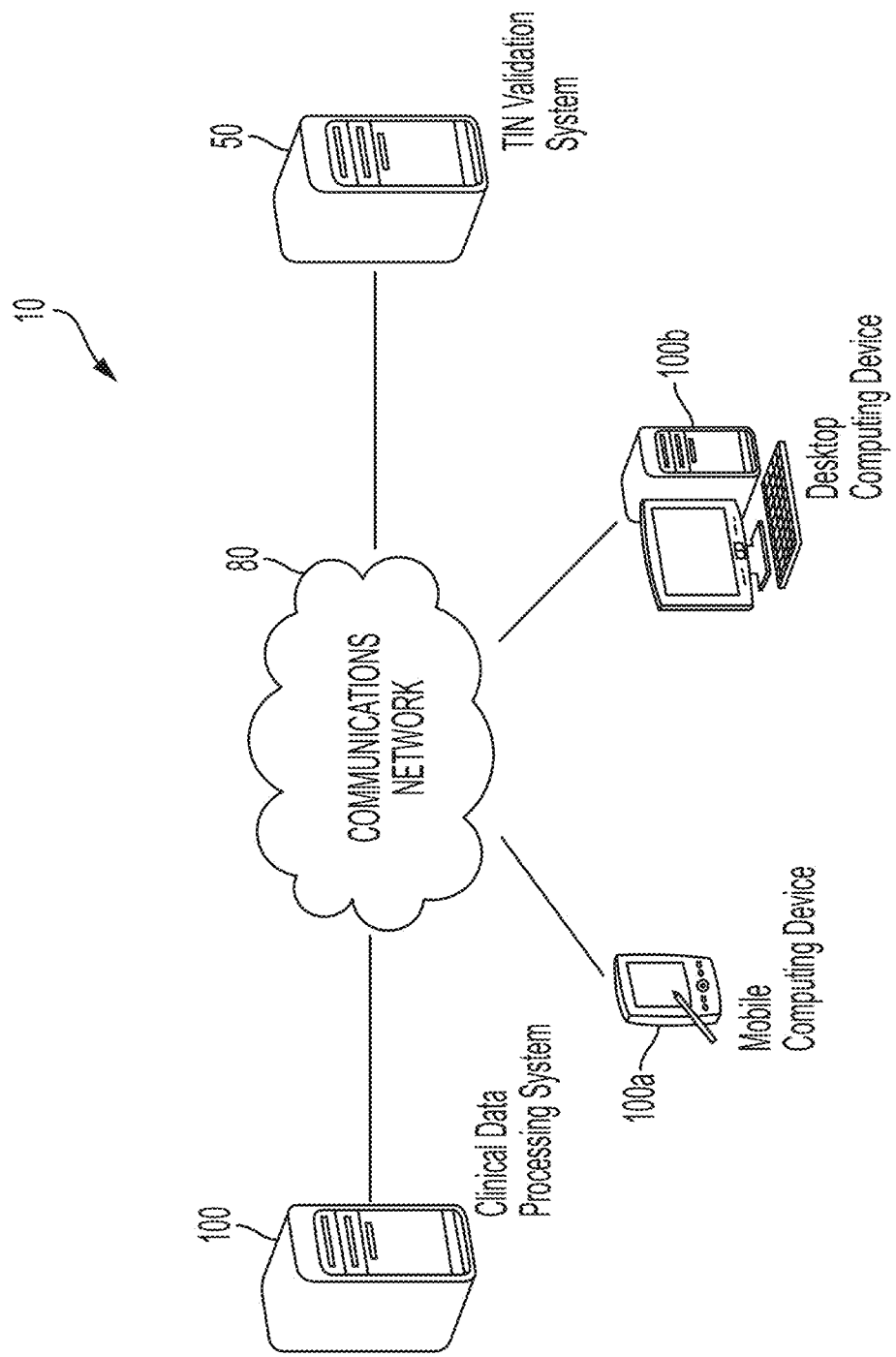
FIG. 1 is a system diagram showing an exemplary network computing environment in which the present invention may be employed.

An exemplary embodiment of the present invention is discussed below for illustrative purposes with reference to the exemplary simplified network environment 10 of FIG. 1. As shown in FIG. 1, the exemplary network environment 10 includes computing devices, such as the Clinical Data Processing System 100 in accordance with the present invention, Mobile Computing Device 100*a* and Personal Computing Device 100*b*. Any suitable computing devices may be used for the purposes described herein. By way of example, the Mobile Computing Device 100a may be a smartphone, a tablet computer, or the like that includes conventional hardware and software and is able to communicate with Clinical Data Processing System 100 via the communications network 80 and execute software applications for the purposes described herein. Similarly, the Personal Computing Device 100b may be a desktop personal computer (PC), laptop computer, or the like that includes conventional hardware and software and is able to communicate via with Clinical Data Processing System 100 the communications network 80 and execute software applications for the purposes described herein. Somewhat, similarly, the Clinical Data Processing System 100 may include conventional hardware and software, but further includes software in accordance with the present invention that configures the Clinical Data Processing System as a special-purpose computing device in accordance with the present invention.

In the exemplary embodiment of FIG. 1, the network computing environment further includes a TIN Validation System 50. Such TIN Validation Systems are operable to validate a Taxpayer Identification Number (TIN), such as a Social Security Number (SSN) or an Employer Identification Number (EIN). More particularly, such systems are operable to receive via the communications network 80 data communications representing a TIN, and to responsively return data communications that either confirm or deny that the identified TIN is valid. Hardware, software, systems, and/or services for performing the functions of the TIN Validation System are well known in the art and beyond the scope of the present invention, and thus are not discussed in detail herein.

In this exemplary embodiment, the Clinical Data Processing System 100 is operatively connected to the computing devices 100a, 100b via a communications network 80, such as the Internet, e.g., via a Virtual Private Network (VPN) connection. Hardware and software for enabling communication of data among such devices via such communications networks are well known in the art and beyond the scope of the present invention, and thus are not discussed in detail herein.

Figure 2:
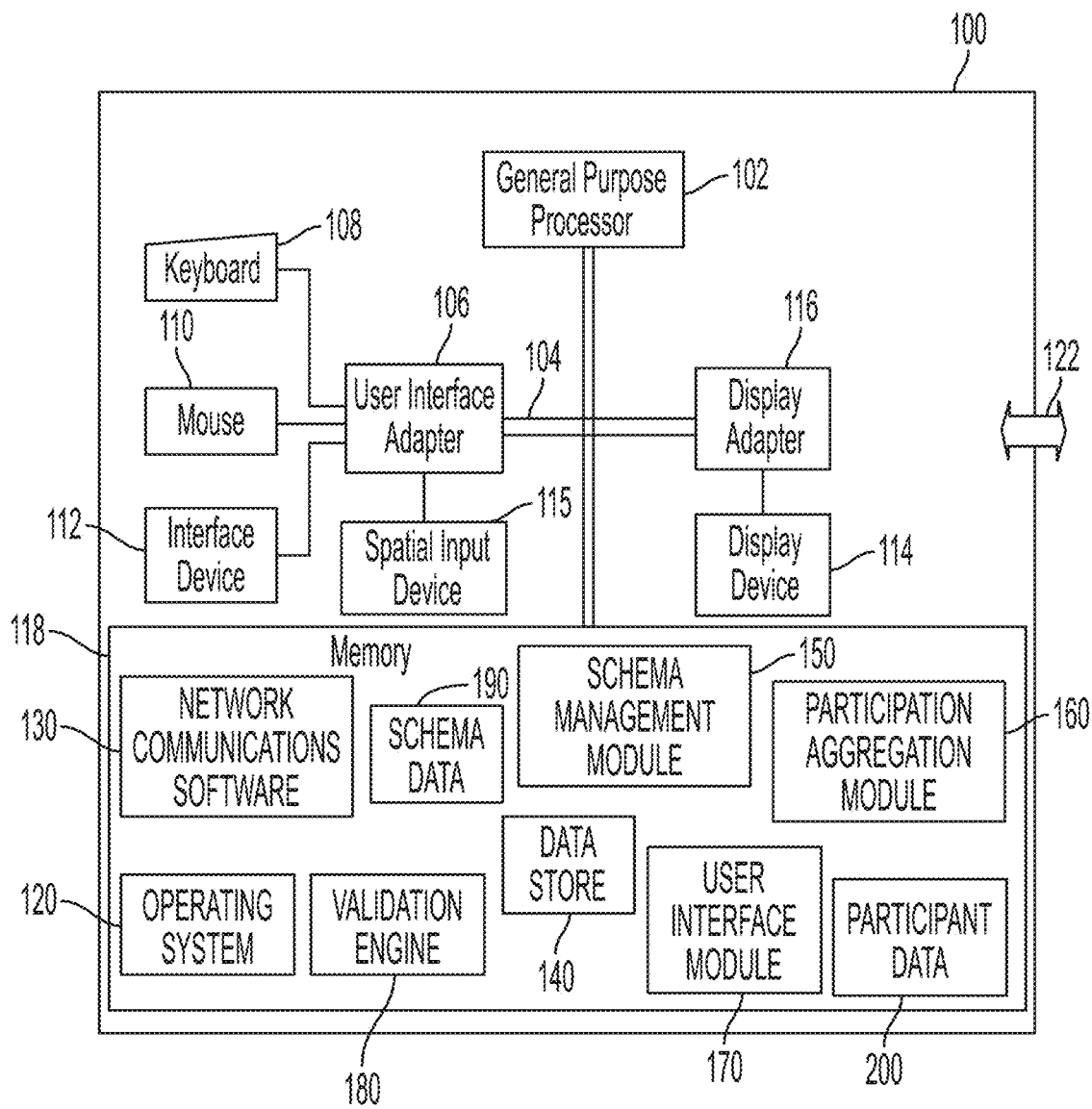
FIG. 2 is a schematic diagram of an exemplary Clinical Data Processing System in accordance with an exemplary embodiment of the present invention.

FIG. 2 is a block diagram showing schematically an exemplary Clinical Data Processing System 100 in accordance with an exemplary embodiment of the present invention. The Clinical Data Processing System 100 is a special-purpose computer system that includes conventional computing hardware storing and executing both conventional software enabling operation of a general purpose computing system, such as operating system software 120 and network communications software 130, and specially-configured computer software (e.g., a software program or code) for configuring the general purpose hardware as a special-purpose computer system including a Schema Management Module 150, a Participation Aggregation Module 160, a User Interface Module 170, a Validation Engine 180, Schema Data 190 and Participant Data 200 for carrying out at least one method in accordance with the present invention. Accordingly, the system and processor may be configured to implement the methods described and illustrated herein. By way of example, the communications software 130 may include conventional web server software, and the operating system software 120 may include iOS, Android, Windows, or Linux software.

Accordingly, the exemplary Clinical Data Processing System 100 of FIG. 2 includes a general-purpose processor, such as a microprocessor (CPU), 102 and a bus 104 employed to connect and enable communication between the processor 102 and the components of the presentation system in accordance with known techniques. The exemplary presentation system 100 includes a user interface adapter 106, which connects the processor 102 via the bus 104 to one or more interface devices, such as a keyboard 108, mouse 110, and/or other interface devices 112, which can be any user interface device, such as a touch sensitive screen, digitized entry pad, etc. The bus 104 also connects a display device 114, such as an LCD screen or monitor, to the processor 102 via a display adapter 116. The bus 104 also connects the processor 102 to memory 118, which can include solid state memory, a hard drive, a diskette drive, a tape drive, etc.

The Clinical Data Processing System 100 may communicate with other computers or networks of computers, for example via a communications channel, network card or other network interface or modem 122. The Clinical Data Processing System 100 may be associated with such other computers in a local area network (LAN) or a wide area network (WAN), and may operate as a server in a client/server arrangement with another computer, etc. Such configurations, as well as the appropriate communications hardware and software, are known in the art.

The Clinical Data Processing System 100 is specially-configured in accordance with the present invention. Accordingly, as shown in FIG. 2, the Clinical Data Processing System 100 includes computer-readable, processor-executable instructions stored in the memory for carrying out the methods described herein. Further, the memory stores certain data, e.g. in databases or other data stores shown logically in FIG. 2 for illustrative purposes, without regard to any particular embodiment in one or more hardware or software components. For example, FIG. 2 shows schematically storage in the memory 118 of the Schema Management Module 150, Participation Aggregation Module 160, User Interface Module 170, Validation Engine 180, e.g., special-purpose software in accordance with the present invention, as well as Schema Data 190 and Participant Data 200. Optionally, other software and/or data may be stored in a corresponding data store 140 of the memory 118.

Figure 3:
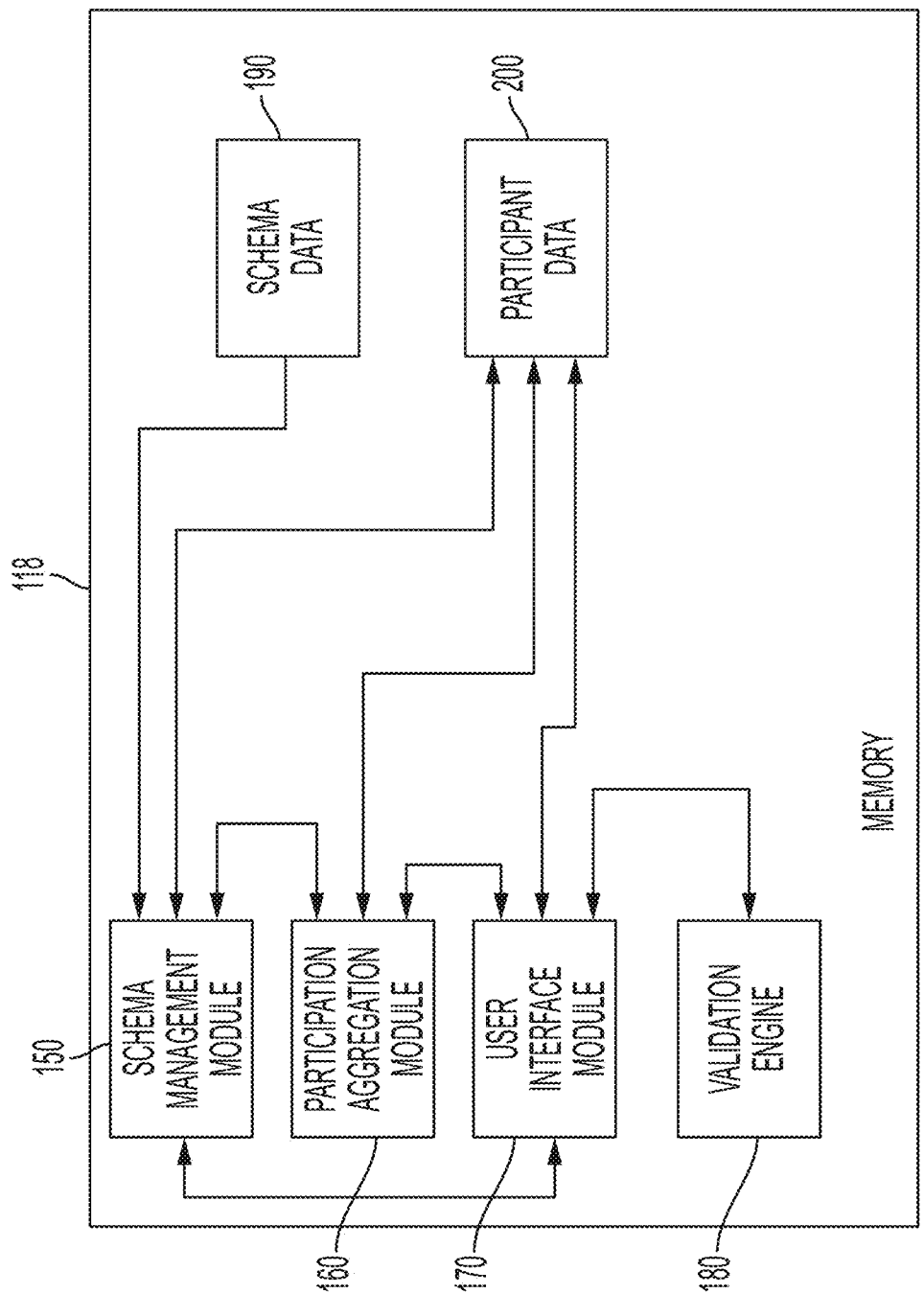
FIG. 3 is a schematic diagram further illustrating exemplary components of the Clinical Data Processing System of FIG. 2.

FIG. 3 is a block diagram illustrating selected logical components of the exemplary Clinical Data Processing System 100 of FIGS. 1 and 2. As will be noted from FIG. 3, the memory 118 of the Clinical Data Processing System 100 includes the Schema Management Module 150, Participation Aggregation Module 160, and User Interface Module 170, as well as Schema Data 190 and Participant Data 200. Optionally, and in the example of FIG. 3, the Clinical Data Processing System 100 further includes a Validation Engine 180. These modules/engine may be implemented primarily by specially-configured software including microprocessor-executable instructions stored in the memory 118 of the Clinical Data Processing System 100. The User Interface Module 170 is configured to display graphical user interface windows in accordance with the present invention via a display device, e.g., of a remote Mobile Computing Device 100a or Personal Computing Device 100b, and to receive input therefrom. The User Interface Module is further configured to read and write clinical trial participant data to and from the Participant Data 200. For example, the clinical trial participant data may include an identification of the participant, an associated clinical trial study, a date of a doctor's visit or other notable event, and a corresponding payment made or due to the participant.

In examples in which the Clinical Data Processing System 100 includes a TIN Validation Engine 180, the User Interface Module is configured to receive TIN information via a user interface and/or from Participant Data 200, to communicate with the Validation Engine 180 (which in turn communications with a conventional TIN Validation System 50 in a conventional manner to validate the TIN), and returns a responsive communication to the User Interface Module 170 indicating whether or not the TIN has been validated, and the User Interface Module may write corresponding data to the Participant Data 200.

The User Interface Module 170 may be further configured to communicate participant participation data and other data to the Participation Aggregation Module 160. The participation data indicates which study the participant is involved in, for example, in response to a participant's arrival at a doctor's office for examination as part of the clinical trial study.

The Participation Aggregation Module 160 is configured to receive participant participation data from the User Interface Module 170 and/or the Participant Data 200, and to aggregate participation data on a per-participant basis. Accordingly, participant participation data received via the User Interface Module 170 for a first clinical trial study will be aggregated with participant participation data received from the Participant Data for the same and other clinical trial studies. In this fashion, payments due to or received by the participant from participation in multiple different clinical trial studies can be aggregated for reporting/taxation/withholding purposes. For example, it might appear that a single payment less than a $600 threshold may not require reporting to the IRS via a form 1009-MISC, however, payments that when aggregated exceed the threshold will require reporting to the IRS via a form 1099-MISC. For determination of appropriate reporting/withholding for the participant, across multiple studies, the Participation Aggregation Module may further communicate with the Schema Management Module 150.

In one embodiment, the Schema Management Module 150 may be configured to receive participant data, such as a participant's residential location, or a clinical trial location, and to reference the Schema Data 190, and to responsively identify a taxation, withholding or other schema applicable to the associated participant. The participant data may be received in whole or in part from the User Interface Module 170 and/or from the Participant Data 200. In another embodiment, an identification of an applicable schema and/or parameters relevant to the schema may be received from the User Interface Module, 170, e.g., in response to data gathered via the User Interface Module 170 in response to schema options displayed by the user Interface Module 170 according to predefined rules. The Schema Data 190 identifies various different taxation/reporting/withholding schema that may apply to various participants. For example, the Schema Data 190 may identify a U.S. federal taxation schema and corresponding data or rules for reporting and/or withholding purposes, as well as taxation schema, etc. for countries outside the U.S. The Schema Management Module 150 determines, as a function of participant or clinical trial study data, which particular schema stored in the Schema Data 190 applies, and applies the associated rules, etc. accordingly. The corresponding reporting/taxation/withholding requirements are communicated back to the Participation Aggregation Module 160.

The Participation Aggregation Module 160 is also responsible for creating reports, and/or transmitting data, so that accurate withholding, or accurate reporting for withholding, etc. purposes, can be provided. In this manner, The Clinical Data Processing system 100 can track payments across multiple clinical studies, applying different withholding requirement schema accurately on a per-participant basis, using a simple user interface that allows an unsophisticated user to engage with the user interface in straightforward fashion—e.g., to simply identify basic participant/clinical study information (such as a participant's residential address, or a clinical trial site location, or an applicable withholding schema), which in turn causes the Clinical Data Processing System 100 to apply the complex and varied withholding requirements accurately on a per-participant basis.

As described in further detail below, Investigators or other users can configure the Clinical Data Processing System 100 with a variety of options specifying exactly how withholding should be applied on a per-participant basis. This is enabled by the Clinical Data Processing System's pre-configuration to cause the User Interface Module 170 to display user-selectable options configured with various different schema. Moreover, when the withholding system is integrated into a clinical payment system, withholding for taxation purposes can be documented in a blinded or unblinded manner for reporting purposes.

Figure 4:
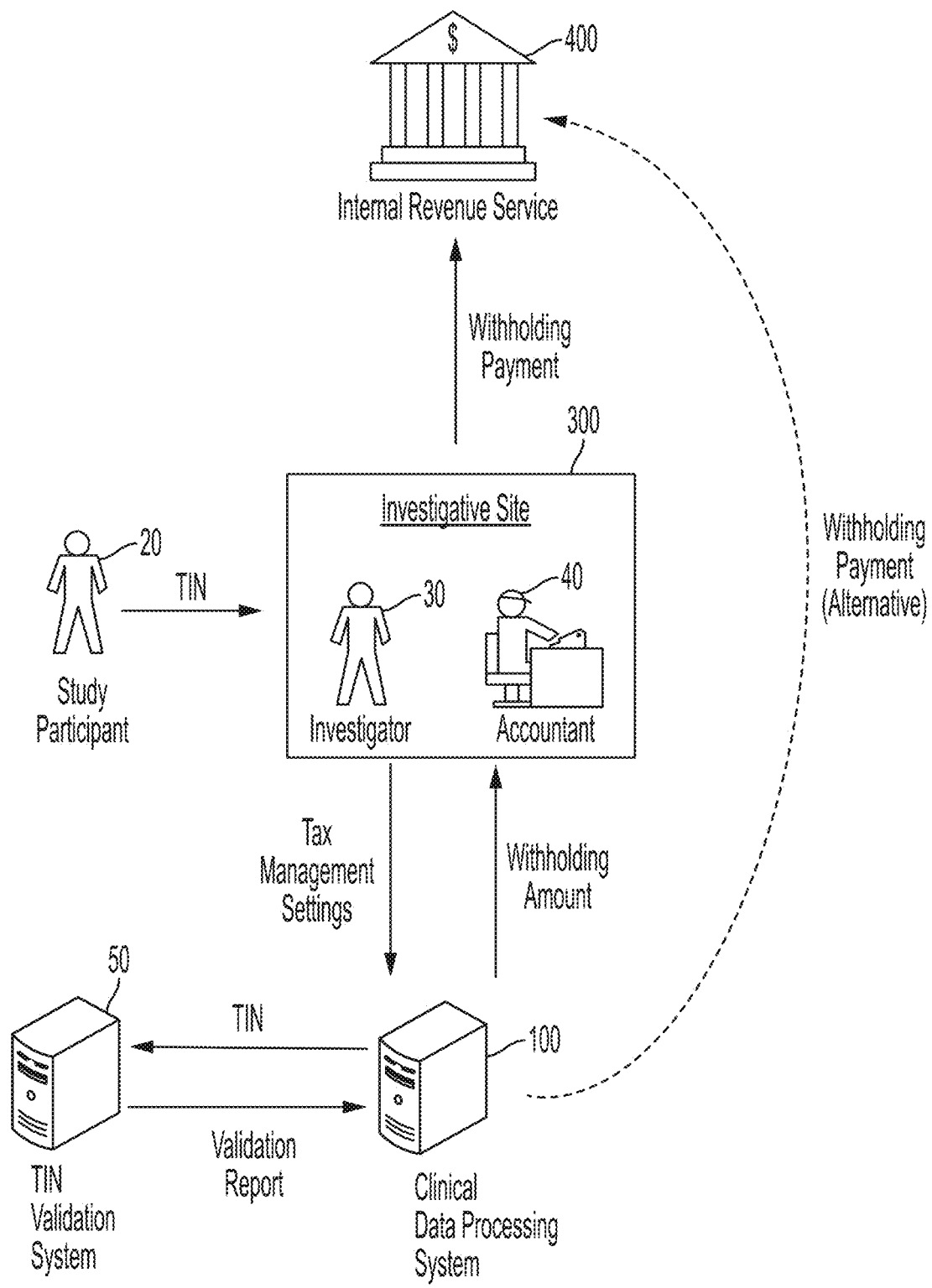
FIG. 4 provides an overview of a system for automating payments for clinical studies, with tax management, according to some embodiments.

FIG. 4 provides an overview of system operation showing schematically interactions with the Clinical Data Processing System 100 for automating withholding and/or payments for clinical studies, with withholding management, according to an exemplary embodiment. The Investigative Site 300 is the entity that conducts a clinical investigation. In this example, the Investigative Site 300 includes an Investigator 30 and an Accountant 40. The Investigator 30 is the individual responsible for conducting the clinical study. For example, for the clinical testing of a drug, the Investigator 30 is the individual under whose direction the drug is administered to the Study Participant 20. In the event a clinical study is conducted by a team of individuals, the Investigator 30 is the responsible leader of the team. The Accountant 40 is a member of the team that issues payments to the Study Participant 220, and ensures that such payments are in compliance with federal regulations and other guidelines regarding clinical studies. For example, where a university is the Investigative Site 300, the Accountant 40 may be the accounting/payroll department of the university itself, or an accounting/payroll department within a certain department within the university.

The Investigative Site 300 collects various information from the Study Participant 20 during the clinical study. Of particular interest to the present disclosure, in the example of FIGS. 1-4, the Investigative Site 300 collects a Taxpayer Identification Number (TIN) from the Study Participant 20. For the purpose of this disclosure, the term TIN refers to any identifier that uniquely identifies an individual for tax purposes. In the U.S., the Internal Revenue Service (IRS) specifies certain identifiers that may be used as a TIN including, a social security number and an individual taxpayer identification number. It should be noted, as described in further detail below, the Clinical Data Processing System 100 does not necessarily require the TIN in order to perform tax management for the Study Participant 100.

The Accountant 40 manages clinical payments by providing input to the Clinical Data Processing System 100. The Clinical Data Processing System 100 may be software executed locally within the computing environment of the Investigative Site 300 or, as shown in the example of FIG. 1, the Clinical Data Processing System 100 operate remotely. In the example of FIG. 1, the Accountant provides input to the Clinical Data Processing System 100 via graphical user interface windows displayed at a computing device 100a, 100b under control of the User Interface Module 170.

The Clinical Data Processing System may communicate with a separate payment processing system, or may include a payment engine responsible for issuing payments to clinical trial Study Participants. For example, the payment engine may be a separate module of the Clinical Data Processing System 100, or may be integrated into the Participation Aggregation Module 150, as in the example of FIG. 3. Because the payment engine and its operation to deliver a defined payment are outside the scope of the present invention, it is not discussed in further detail here.

The Clinical Data Processing System 100 allows the Investigative Site 300 to maintain records for one or more clinical studies. Payment requests may be received at the Clinical Data Processing System 100 from the Investigative Site 300 and possibly other Investigative Sites associated with Study Participant activity. For each Study Participant 20 that is participating in the clinical study, the Clinical Data Processing System 100 may store a unique Study Participant ID, a de-identified subject ID, and the Study Participant's TIN (if available). This may be performed by the Investigator's 30 or Accountant's 40 use of a Mobile Computing Device 100a or Personal Computing Device 100b to provide input to the Clinical Data Processing System 100. In particular, the User Interface Module 170 of the Clinical Data Processing System 100 causes graphical user interface windows to be displayed at the Mobile Computing Device 100a and/or the Personal Computing Device 100b to display to and gather information from the Investigator 30 or Accountant 40 interfacing with the Clinical Data Processing System 100. Received participant data is stored as Participant Data 200.

Once the Study Participant 20 has been registered with the Clinical Data Processing System 100 by entering participant data into the displayed graphical user interface windows, the User Interface Module 170 causes display of graphical user interface windows for gathering participant-specific withholding information. This may be done in a generic manner common to all participants as the result of preconfigured rules of the User Interface Module 170, or may be performed in a manner customized for each participant on a per-participant basis as a function of an applicable schema as determined by the Schema Management Module, e.g., based on participant information received via the User Interface Module 170 and/or schema information received from the Schema Data 200 and/or based on predefined rules of the Schema Management Module 150. Investigator 30 or other staff at the Investigative Site 300 may specify withholding data via the graphical user interface windows that enable the Clinical Data Processing System to reference the Schema Data 190 to identify appropriate reporting/taxation/withholding rules for the Study Participant 20. These settings and exemplary graphical user interface windows are described in detail below with reference to FIGS. 5A-5J. Briefly, the Clinical Data Processing System 100 displays graphical user interface windows that allow the Investigative Site 300 to specify whether to apply withholding or not, the withholding amount, and how withholding should be applied, by entering appropriate data via the graphical user interface windows. The entries of the Investigative Site 300 via graphical user interface windows displayed at the Mobile Computing Device 100a or Personal Computing Device 100b may be received the User Interface Module 170 and Schema Management Module 150 to determine the appropriate withholding rules applicable to the participant, and by the Participation Aggregation module 160 to determine appropriate withholding for the participant in view of the participant's participation across multiple clinical trial studies, as reflected in the Participant Data 200.

Use of the TIN may be optional in some embodiments; that is, tax management may be performed with or without the TIN for Study Participant. However, where the TIN is supplied via the graphical user interface, the TIN is received by the User Interface Module 170 and the Clinical Data Processing System 100 may use an external TIN Validation Service 50 that is contacted via the Validation Engine 180 to confirm that the TIN is valid and associated with the Study Participant 20.

Payment requests from the Investigative Site 300 are processed, e.g., at the Clinical Data Processing System 100, and payments that conform to predefined compensation guidelines for the clinical study are approved via electronic authorization. In certain embodiments, the Clinical Data Processing System 100 informs the Investigative Site 300 (or separate payment system) of an accurately-determined amount of withholding is appropriate for the Study Participant 20. This is performed by the Participation Aggregation Module 160, after identifying the applicable withholding schema and examining the participant's participation across one or more clinical trial studies, as reflected in the Participant Data 200, and may be communicated by transmitting a report to the Investigative Site, displaying data via the Mobile Computing Device 100a or Personal Computing Device 100b, etc. In certain embodiments, the Investigative Site 300 then uses this information to issue an accurate withholding tax payment to the tax authority, in this case the Internal Revenue Service (IRS) 40. In some embodiments, the Investigative Site 300 or the Clinical Data Processing System 100 may be configured to automatedly handle payment operations (e.g., via an automated ACH/wire transfer), including payment of the withholding tax payment directly to the IRS 40, as represented in FIG. 4.

The Clinical Data Processing System 100 may also generate blinded payment reports for electronic delivery to the sponsor. The payment reports may show, for example, the de-identified subject ID for each approved payment, the payment amounts for each approved payment, and the accurate amount of withholding. This reporting may be performed by the Participation Aggregation Module 160 to reflect one or more payments to the participant corresponding to one or more clinical trial studies, as reflected in the Participant Data 200.

FIGS. 5A-5K illustrate an exemplary graphical user interface windows that may be displayed by the Clinical Data Processing System 100 (at the Mobile Computing Device 100a to Personal Computing Device 100b), e.g., under control of the User Interface Module 170, when performing tax management functions. These graphical user interfaces may be accessed, for example, as web pages via a web browser on a desktop computer or a mobile device.

Figure 5A:
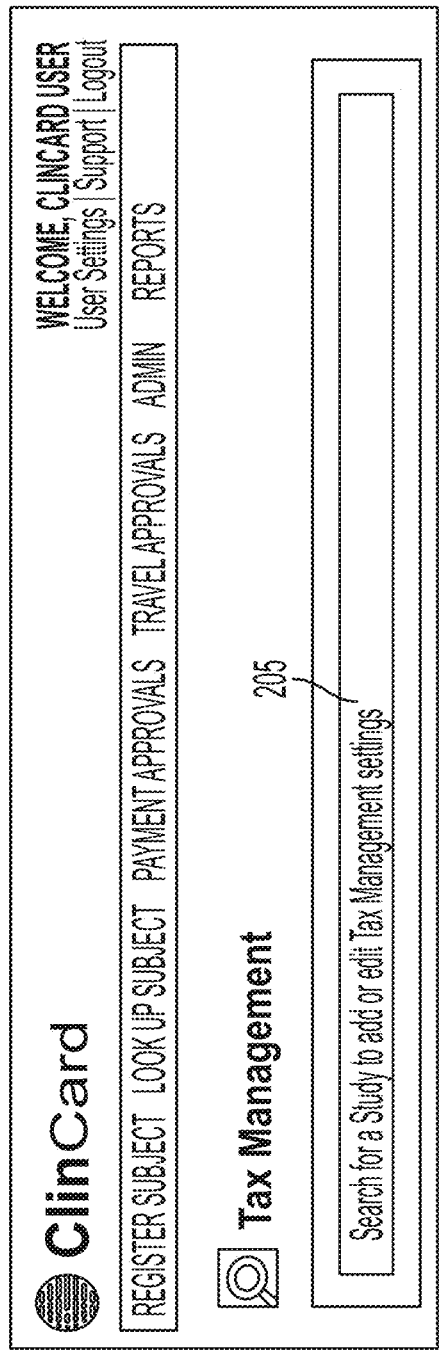
Figure 5B:
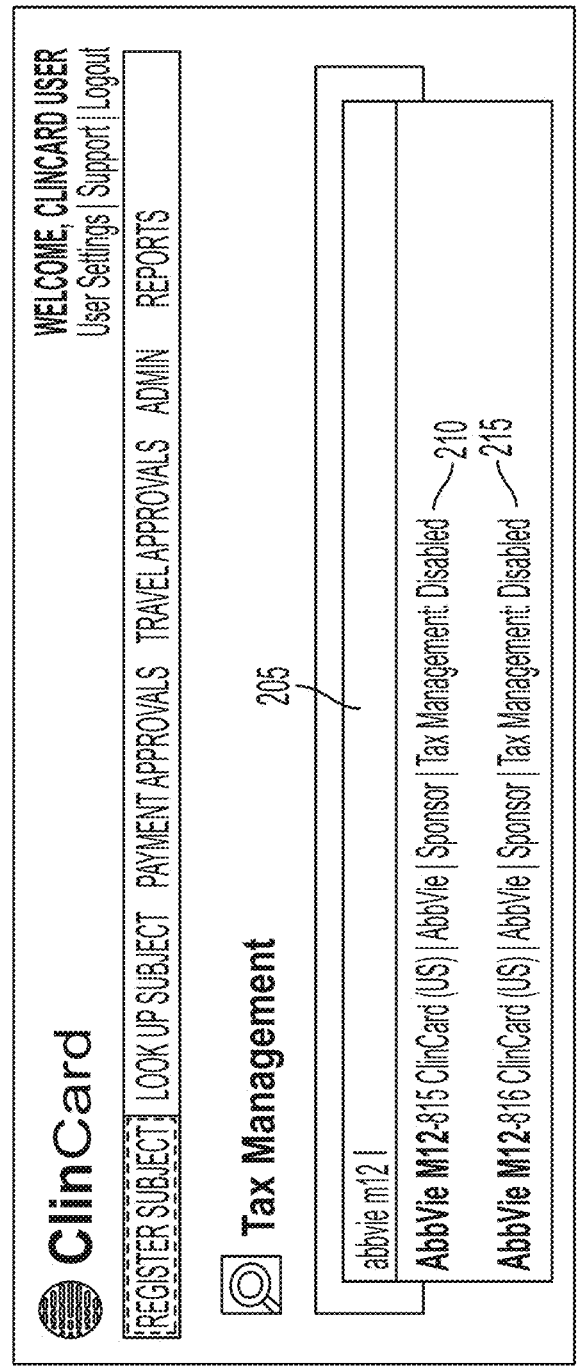

FIG. 5A shows an exemplary graphical user interface window caused to be displayed at a computing device 100a, 100b under control of the User Interface Module 170 of the Clinical Data Processing System 100. The exemplary window of FIG. 5A includes a search field 205 that allows a user to search for a study to add or edit tax management settings. FIG. 5B shows a predictive search feature of the tax management interface. In this example, "abbvie m12" is typed into the search field 205 and text corresponding to records for AbbVie M12-815 and AbbVie M12-816 are shown as selectable links 210 and 215, respectively. In this case, a search has been performed for records previously stored containing the text "abbvie m12." Methods for performing predictive search are generally understood in the art and, thus, these techniques are not discussed in detail herein. In this example, these values are specified in U.S. dollars, but the monetary values could be adjusted, as needed, based on currency settings.

Figure 5C:
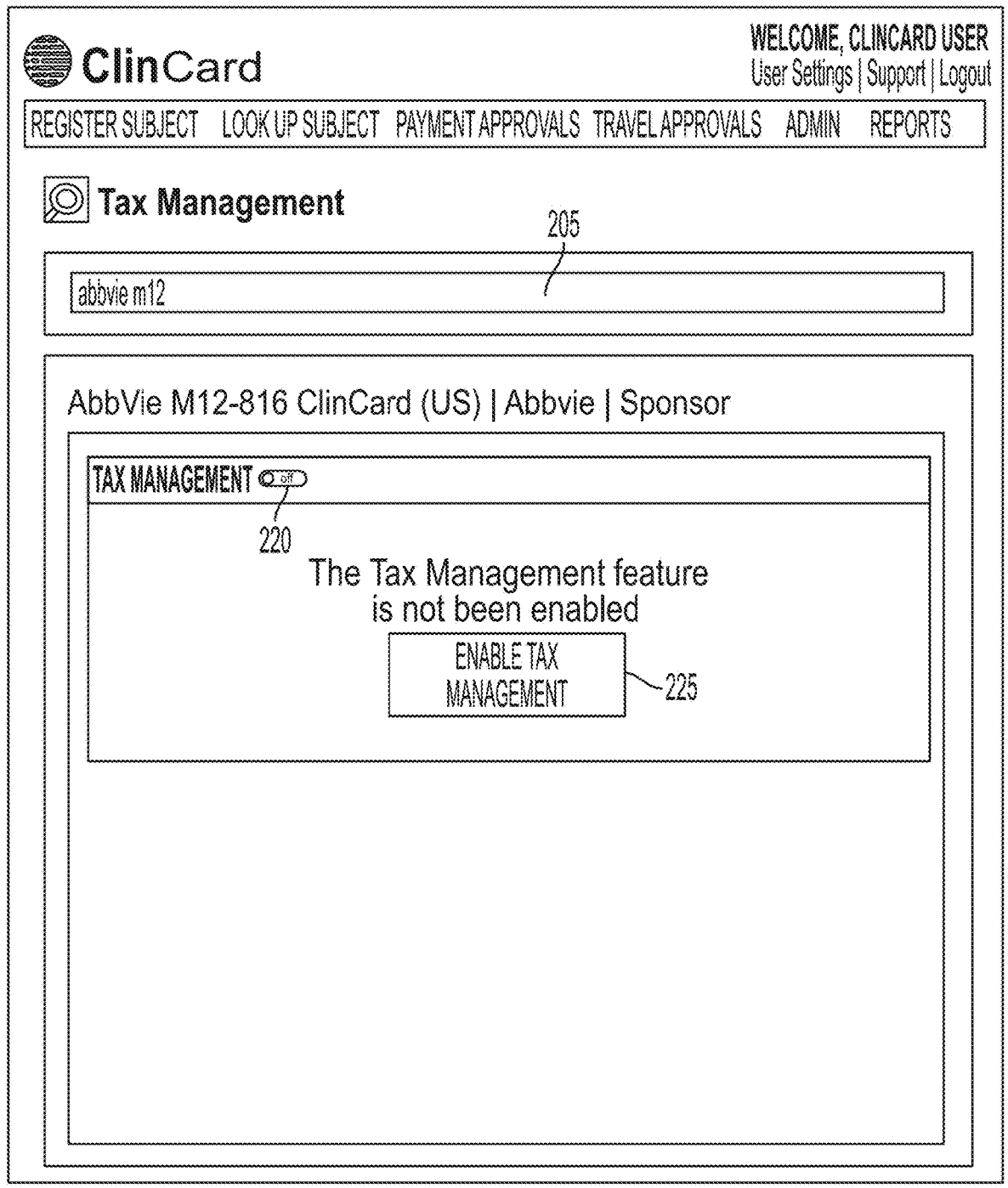

FIG. 5C shows an exemplary Study Details graphical user interface window, which contains a Tax Management section. In this example, a user-selectable link 215 corresponding to "AbbVie M12-816 ClinCard (US)" was selected from the interface shown in FIG. 5B.

Figure 5D:
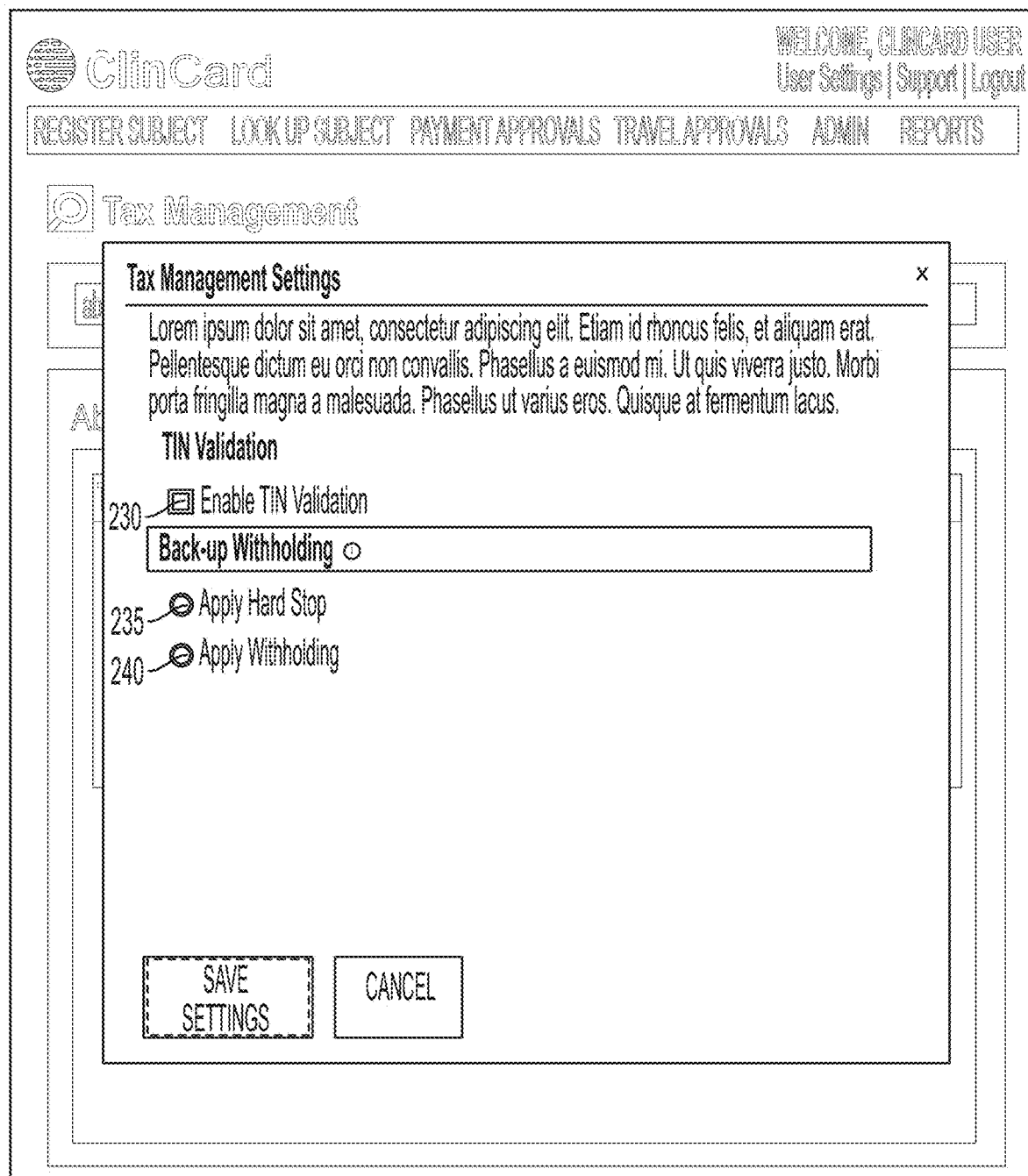

In response to a user's selection of the "Enable Tax Management" button 225 or the "On/Off" toggle 220 next to the "Tax Management" heading in the graphical user interface window of FIG. 5C, the User Interface Module 170 displays a tax management modal graphical user interface window containing various relevant settings, as shown in FIG. 5D. In FIG. 5D, a TIN validation option box 230 provides the user with the option to validate the TIN of the Study Participant (see FIGS. 1 and 4). A user's entry of input to the Clinical Data Processing System 100 causing selection of this option initiate's operation of the Validation Engine 180 to validate and TIN received via the user Interface Module 170 by contacting a TIN validation server or services.

In the example of FIG. 5D, the User Interface Module 170 has also caused display in the graphical user interface window of user-selection options corresponding to an applicable taxation schema. In particular, the exemplary tax management modal window also includes a back-up withholding section that includes two user-selectable radio buttons 235 and 240 corresponding to options for an "Apply Hard Stop" and an "Apply Withholding," respectively. These options are relevant to the US federal taxation schema, and the $600 threshold discussed above, and are displayed automatedly as appropriate for a particular participant according to rules of the Clinical Data Processing System 100. These options may be displayed as user-selectable options by the user Interface Module 170 based on information contained in the Schema Data 190 and/or Participant Data 200, under control of the Schema Management Module 150, that indicates the applicable withholding schema that makes these options relevant to withholding/tax management for the participant. Further, information gathered by the User Interface Module 170, may be stored in the Participant Data 200, and be communicated to one or more of the Schema Management Module 150 and/or the Participation Aggregation Module 160. Each of these options is described in further detail in the paragraphs that follow.

Figure 5E:
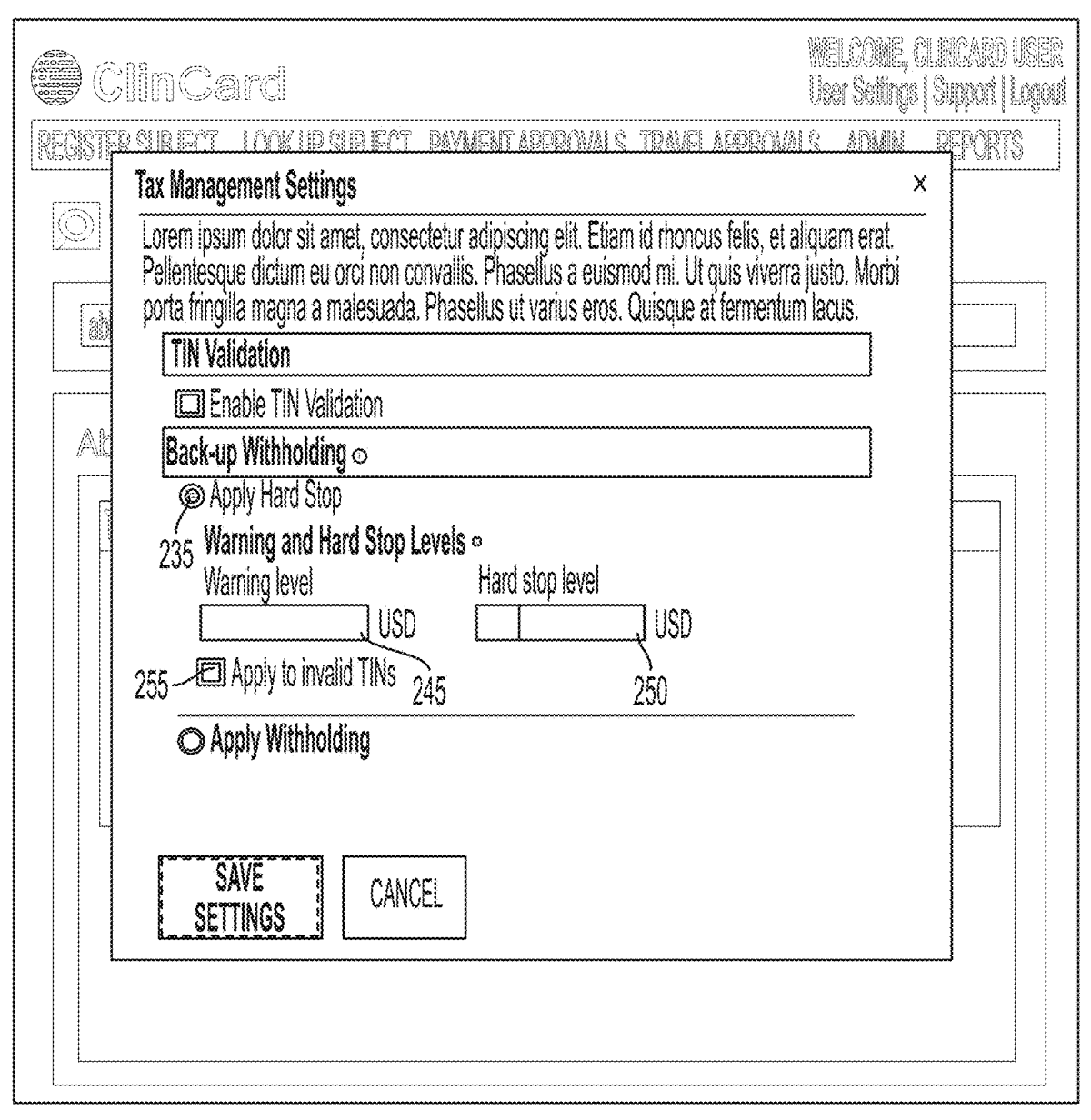

In FIG. 5E, the "Apply Hard Stop" radio button 235 has been selected. Accordingly, the User Interface Module 170 causes display to the user of two input textboxes 245, 250 for setting hard stop levels. The User Interface Module 170 is caused to display these options as user-selectable options based on information contained in the Schema Data 190 and/or Participant Data 200, under control of the Schema Management Module 150, that indicates the applicable withholding schema that makes these options relevant to withholding/tax management for the participant. Further, information gathered by the User Interface Module 170, may be stored in the Participant Data 200, and be communicated to one or more of the Schema Management Module 150 and/or the Participation Aggregation Module 160.

According to predetermined rules of the Clinical Data Processing System, with the "Apply Hard Stop" setting, the Clinical Data Processing System 100 prevents the making of payments to the Study Participant if a valid TIN has not been provided, and/or if the payment would push the participant's YTD Earnings above a predetermined hard stop level as specified in text box 250, in order to better comply with applicable taxation/withholding requirements relevant to a US federal taxation schema, as discussed above. Optionally, the user may specify a warning level 245 for providing the user a notification that the Study Participant is approaching the hard stop level. For example, the user may specify $500 and $600 as the warning and hard stop level, respectively. Once aggregated payments (aggregated across multiple studies if appropriate) to the Study Participant reach or exceed $500, the Clinical Data Processing System programmatically issues a notification to the user that the study subject is approaching the hard stop level. This checking and enforcement of the hard stop functionality, and notification, is performed by the Participation Aggregation Module 160 in accordance with predefined rules of the module, with reference to prior participant information stored as Participant Data 200. This notification may be provided, for example, as an item in the study subject's record (see, FIG. 6) or in a message transmitted to the user. If a later payment to the Study Participant would result in over $600 in payments to the Study Participant, the Participation Aggregation Module 160 of the Clinical Data Processing System 100 will hold back the payment to the study subject and provide a notification to the user that the hard stop level has been reached.

In this example, the tax management modal further includes a checkbox 255 allowing the user to specify whether withholding should be applied. That is, after validation, if a TIN is determined to be valid, hard stop functionality need not be used, and payments may be processed. If, however, a TIN is determined to be invalid, or a valid TIN has not been provided, then the hard stop functionality may be used to avoid the need to withhold and/or remit withholding payments, as it will prevent the making of payments triggering such obligations. In this circumstance, the Validation Engine 180 may cause payments to remain pending until a valid TIN is provided.

Figure 5F:
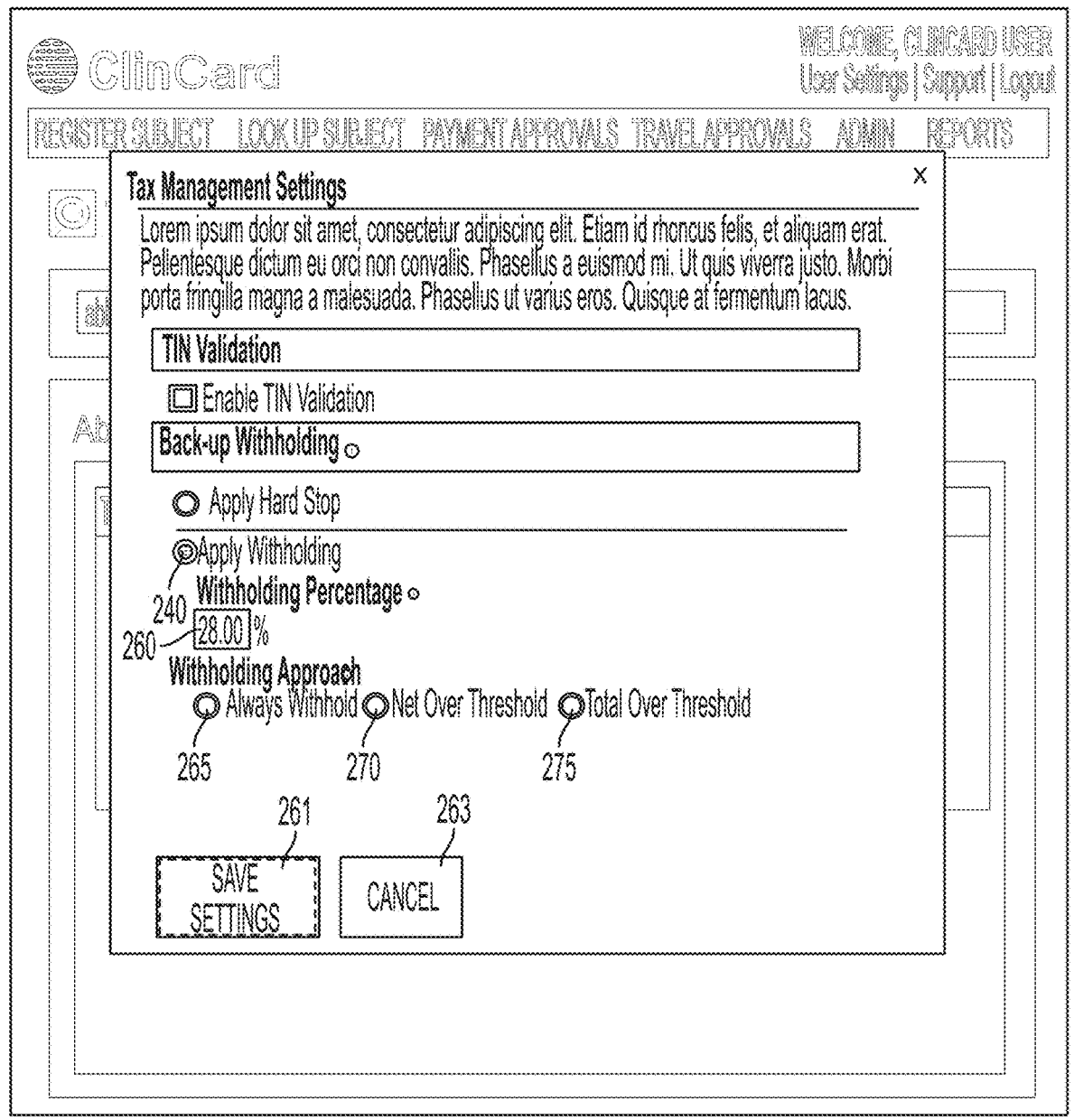

In FIG. 5F, the "Apply Withholding" option has been selected using radio button 240 as the result of user input via a computing device 100a, 100b. This option, presented by the User Interface Module 170, is operable to cause a percentage of the payment amount to be withheld from the Study Participant for tax purposes. The User Interface Module 170 is caused to display these options as user-selectable options based on information contained in the Schema Data 190 and/or Participant Data 200, under control of the Schema Management Module 150, that indicates the applicable withholding schema that makes these options relevant to withholding/tax management for the participant. Further, information gathered by the User Interface Module 170, may be stored in the Participant Data 200, and be communicated to one or more of the Schema Management Module 150 and/or the Participation Aggregation Module 160.

In accordance with selection of this option, a textbox 260 allows the user to specify a particular percentage of the subject's payment that should be subject to withholding (e.g., 28%). This percentage is withheld from payouts to the Study Participant for tax participant. This may be accomplished by a payment module or system, and may be communicated to the payment module or system, e.g., by the Schema Management module 150. In some embodiments, a country-specific, default value may be specified in the textbox 260, as determined by the pre-stored Schema data and/or the Schema Management Module 150, and as displayed by the User Interface Module 170. For example, in the U.S., the standard back-up withholding may be set to 28% in accordance with the US federal taxation schema. Payments to non-resident aliens in a country may be subject to a fixed withholding. For example, in the U.S., payments to non-resident aliens are subject to 30% federal income tax withholding, as provided for in the US federal taxation schema. For the purposes of this discussion, a non-resident alien is any individual that is not a U.S. citizen, permanent resident alien, or resident aliens for tax purposes. These options may be displayed by the User Interface Module 170 as the result of information gathered by the Schema Management Module 150, and from the Schema Data 190, based on rules configured into the Schema Management Module 150.

Figure 5G:

The "Apply Withholding" option is also operable to cause a user-specified approach for withholding to be applied. In this example, there are three radio buttons 265, 270, 275. The first radio button 265 is labeled "Always Withhold" and when selected, causes the Schema Management Module 150 (or payment module/system) to withhold a particular percentage set in the textbox 260 from every payment to the Study Participant. The second radio button 270, labeled "Net Over Threshold," when selected, causes the Schema Management Module 150 (or payment module/system) to apply the withholding percentage set in textbox 260 only to amounts paid to the Study Participant if those amounts are above a predetermined withholding threshold in a single year. As shown in FIG. 5G, selecting the second radio button 270, causes a text box 280 to be displayed allowing the user to specify the withholding threshold. Additionally, a second text box 285 allows the user to specify a warning level so that the user is provided a notification as the Study Participant's withholding approaches the threshold. The third radio button 275 shown in FIG. 5F, when selected, causes the Schema Management Module 150 (or payment module/system) to use a "Total Over Thresholding" withholding approach. With this approach, the withholding percentage set in textbox 260 is applied to the last payment that pushes the Study Participant YTD Earnings above a withholding threshold (set in a manner similar to the manner discussed above with respect to FIG. 5G). Additionally, the withholding percentage will be applied to all payments for the remainder of the year.

Clicking the "Save Settings" button 261 causes the system to save the tax management settings linked to Study Participant in the Participant Data 200 and close the tax management modal. Conversely, clicking the "Cancel" button 263 causes the system to ignore any changes to the tax management settings and close the tax management modal. Accordingly, it should be appreciated that a simple, easy-to-understand graphical user interface is provided by the User Interface Module 170 that enables a user to provide simple input and resultingly causes the Clinical Data Processing System 100 to perform complex clinical trial administration-related functions.

Figure 5H:
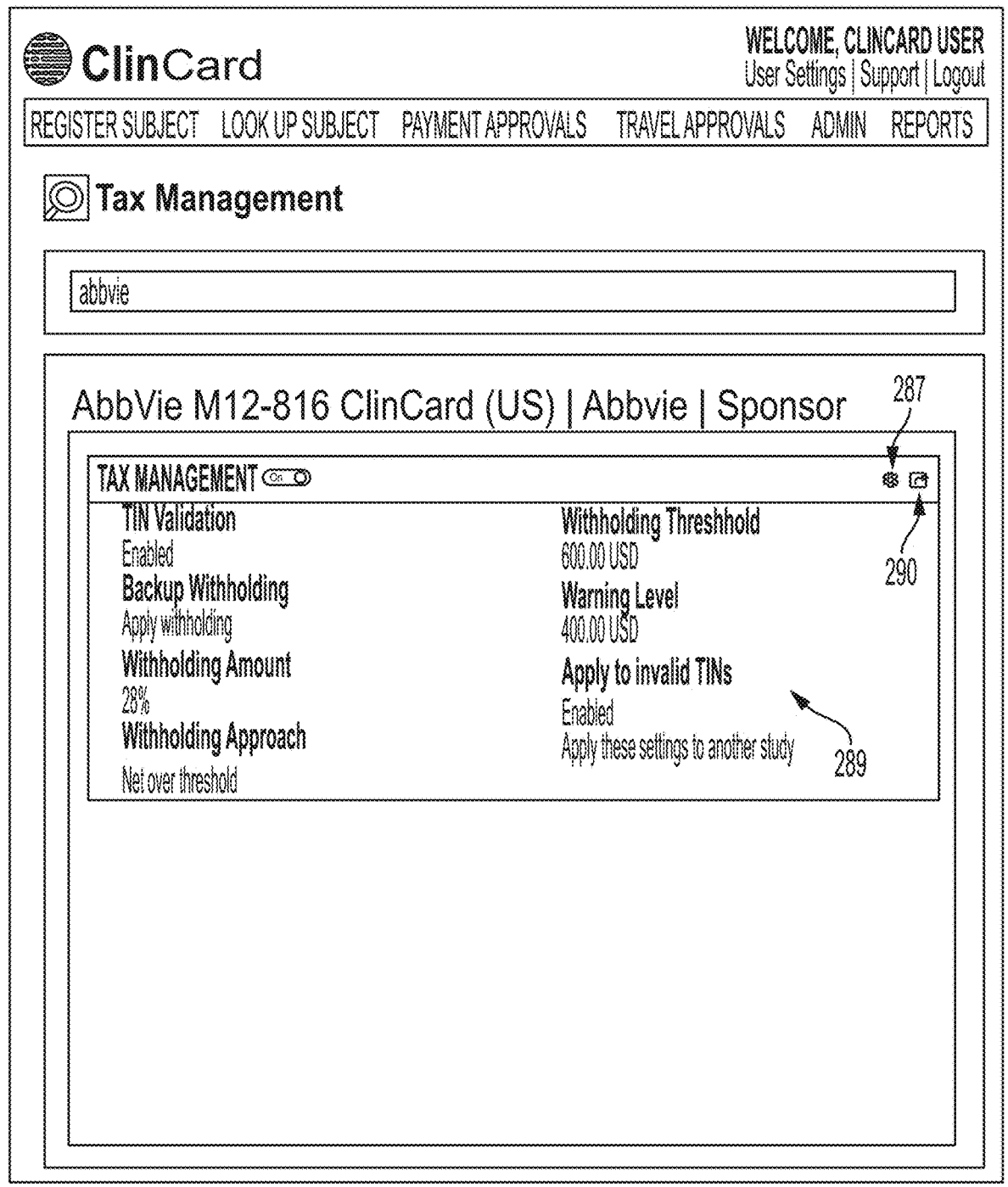
Figure 5I:
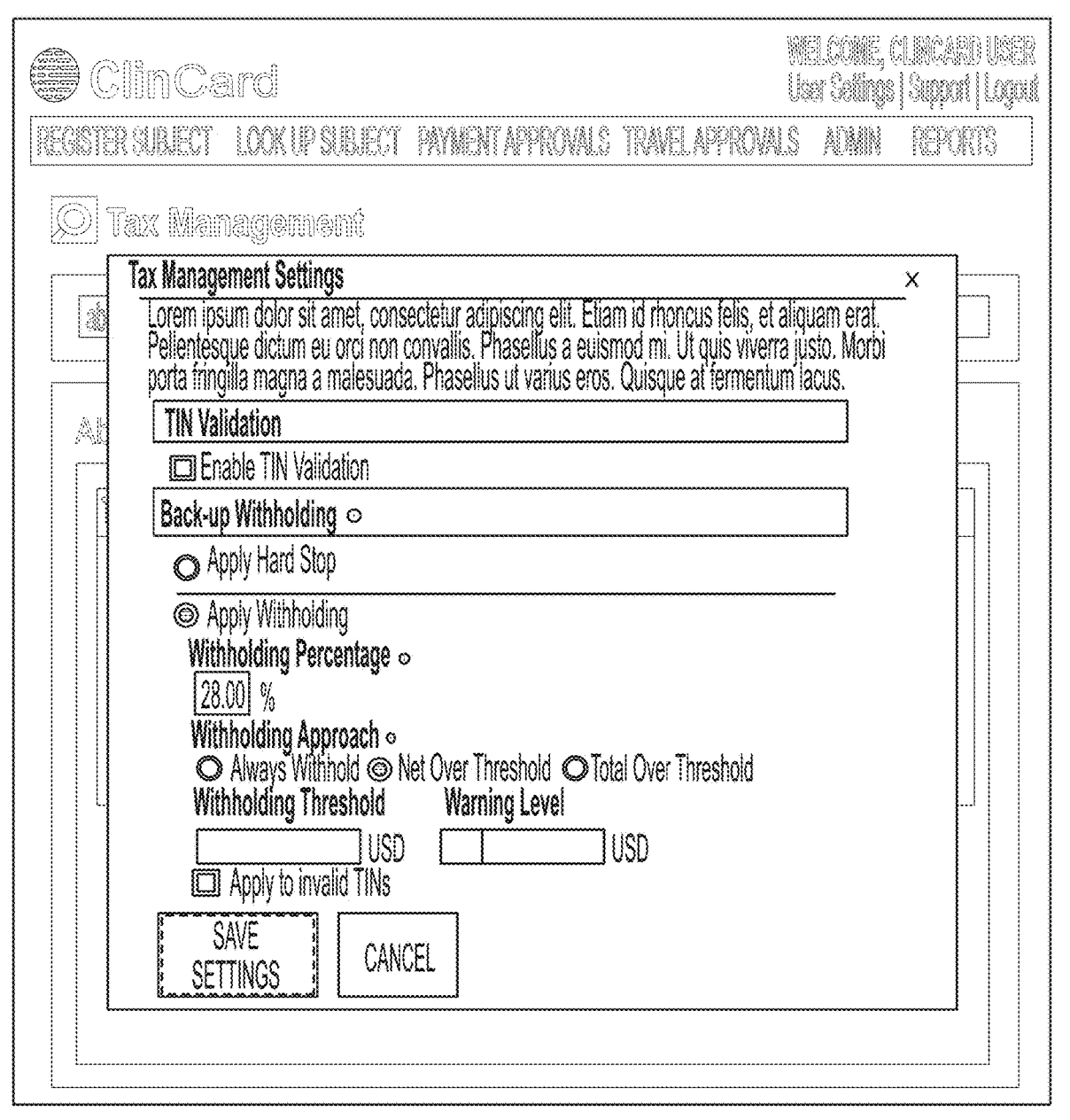
Figure 5J:
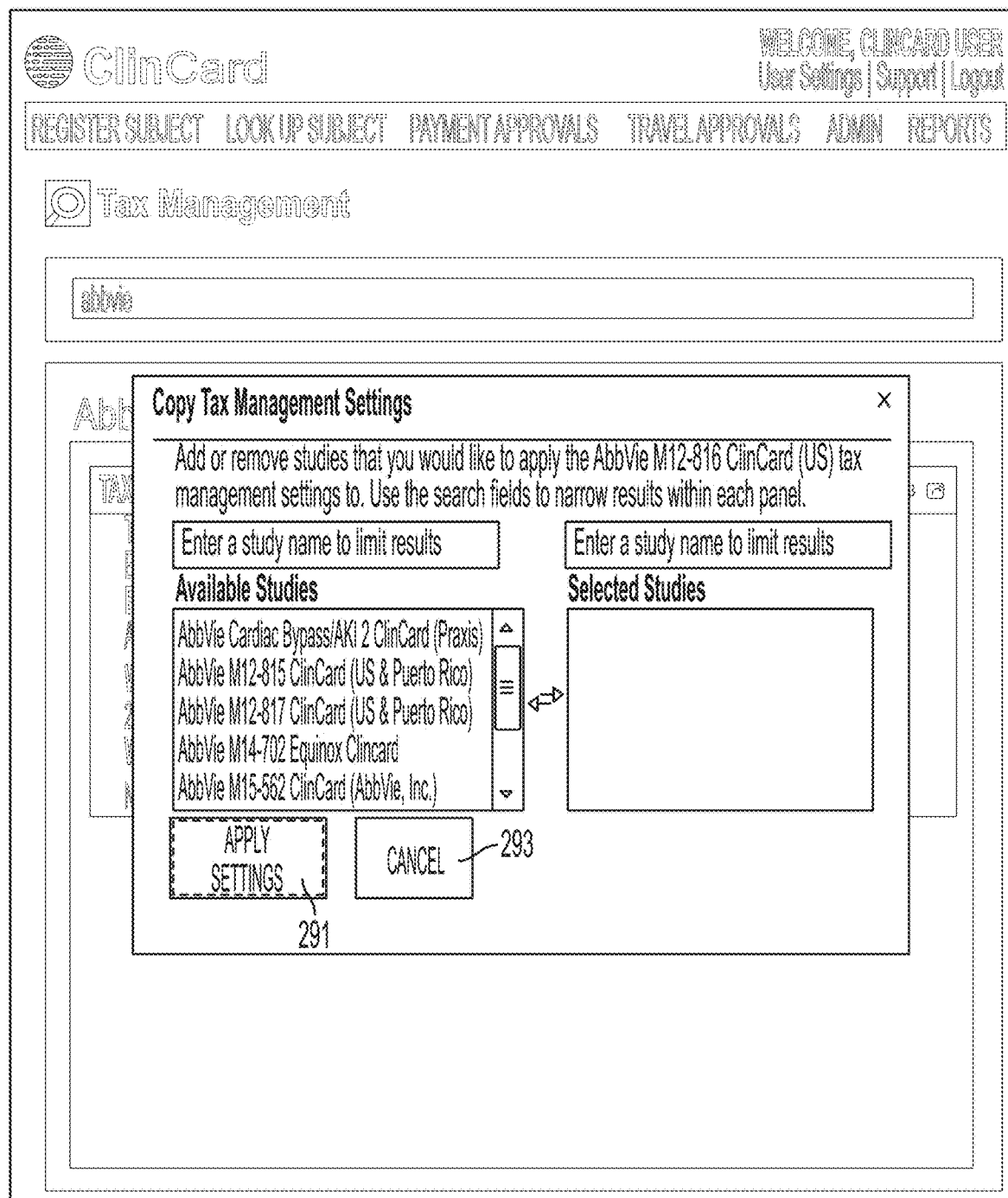

Once the tax management options have been configured and the modal has closed, the tax management interface displays all of the settings just applied in a read-only format as shown in FIG. 5H. Clicking the gear icon 287 on the right side of the tax management section will display the modal containing the active tax management settings as shown in FIG. 5I. The user can use the "Apply these settings to another study" link 289 or the icon 290 in the far right of the section header in FIG. 5H to access the copy tax management settings interface shown in FIG. 5J. With the copy tax management settings interface, the use can apply the Study Participant's tax management to other studies. The available studies are listed on the left hand side of the copy tax management settings interface. If the user selects a study and clicks on the arrow icon, the study is listed in the "selected studies" section on the right hand side of the copy tax management settings interface. Once all the desired studies have been selected, the user can click the "Apply Settings" button 291 to copy the settings to the selected studies. Alternatively, clicking the "Cancel" button 293 causes the system to disregard any changes. Accordingly, it should be appreciated that the User' Interface Module 170 provides a simple, easy-to-understand graphical user interface that enables a user to provide complex clinical trial administration-related functions in a simple and streamlined fashion.

Figure 5K:
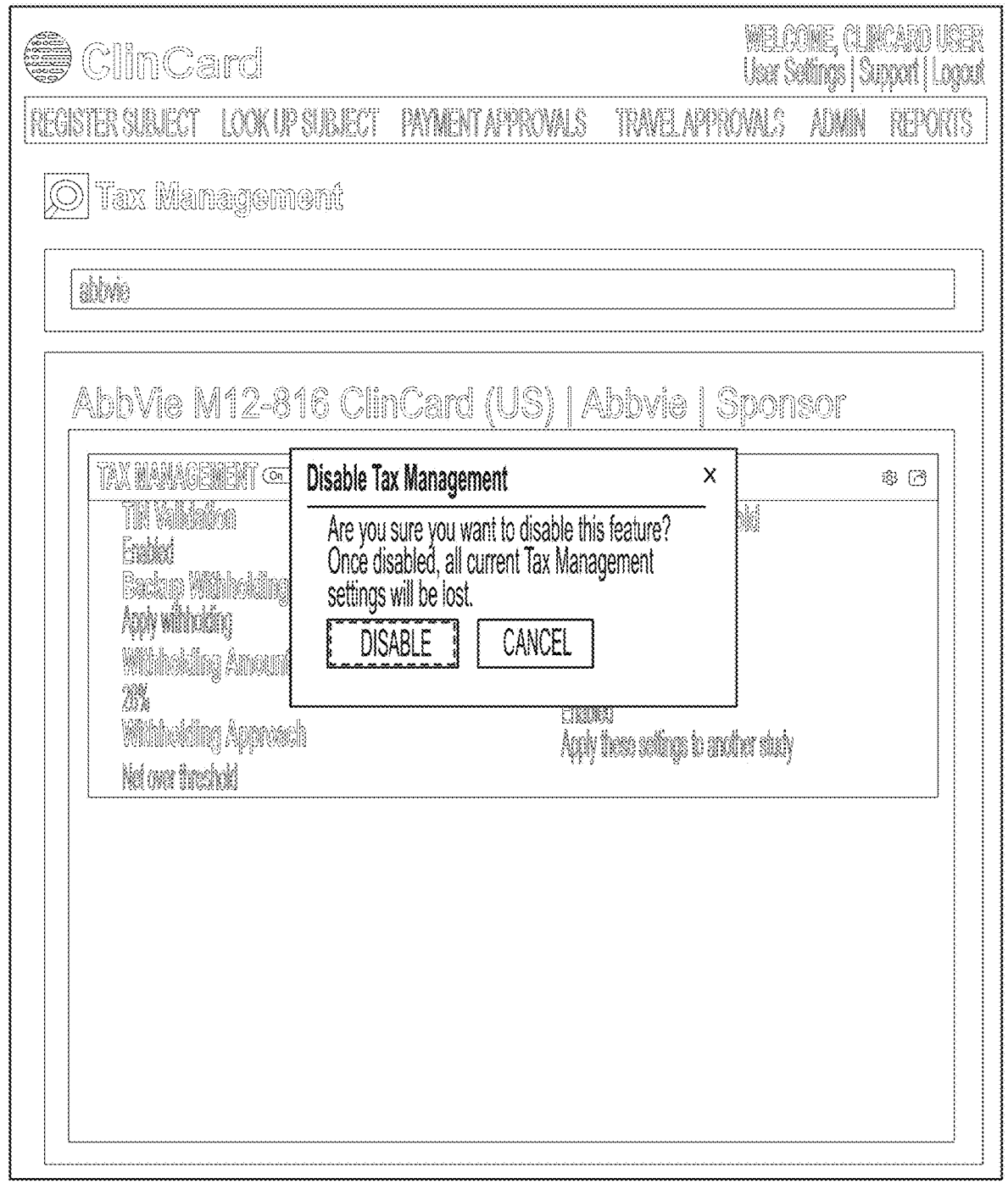

If a user chooses to disable the tax management settings using the "On/Off" toggle 220 (see e.g., FIG. 5C), the user may be presented with a confirmation modal informing them that all current settings will be lost. An example confirmation modal is shown in FIG. 5K. In some embodiments, a page-level alert may also be displayed confirming that the TIN settings have been disabled.

Figure 6:
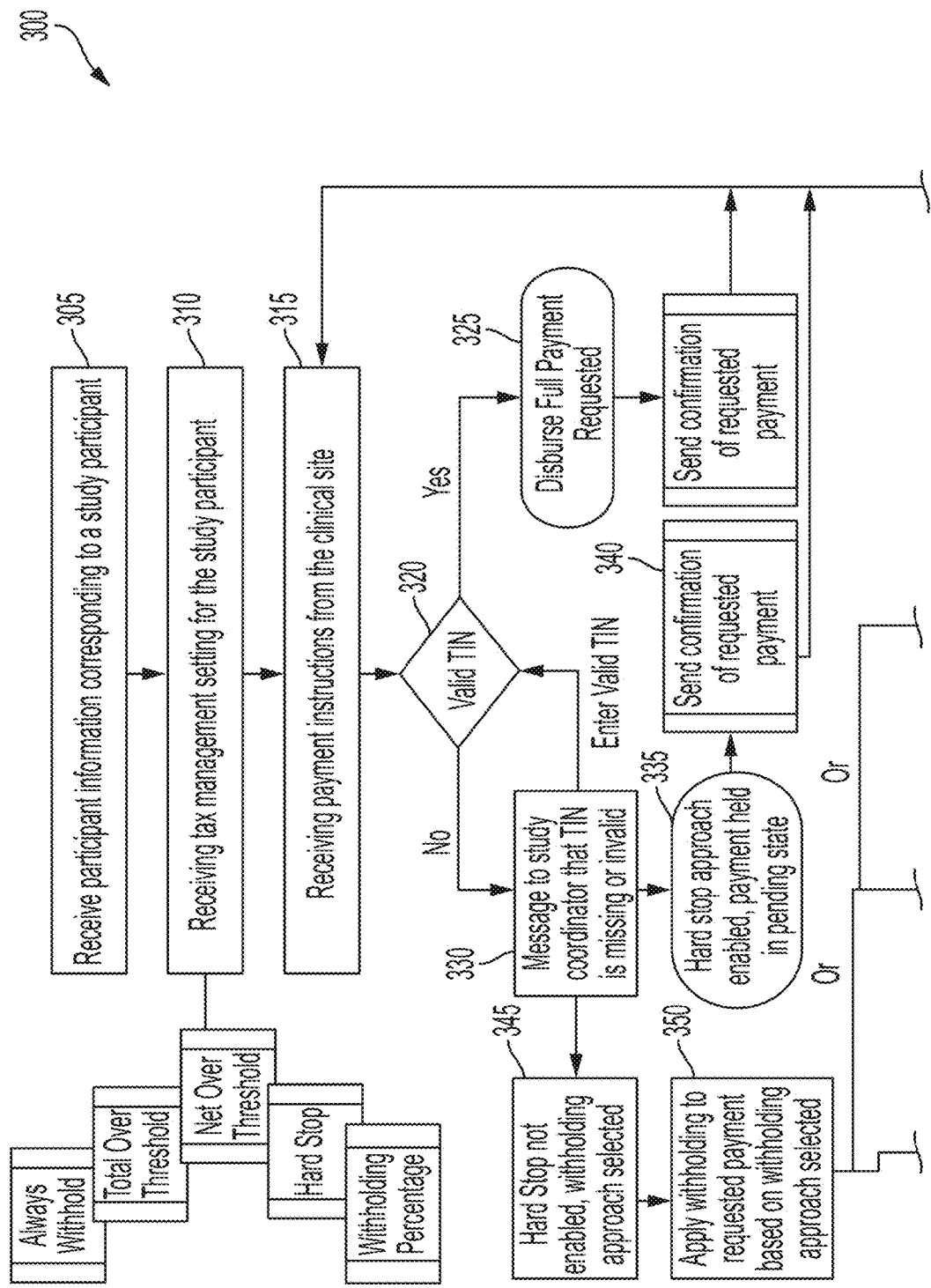
FIG. 6 provides a flowchart illustrating a process of performing tax management of clinical study payments, according to some embodiments.
Figure 7:
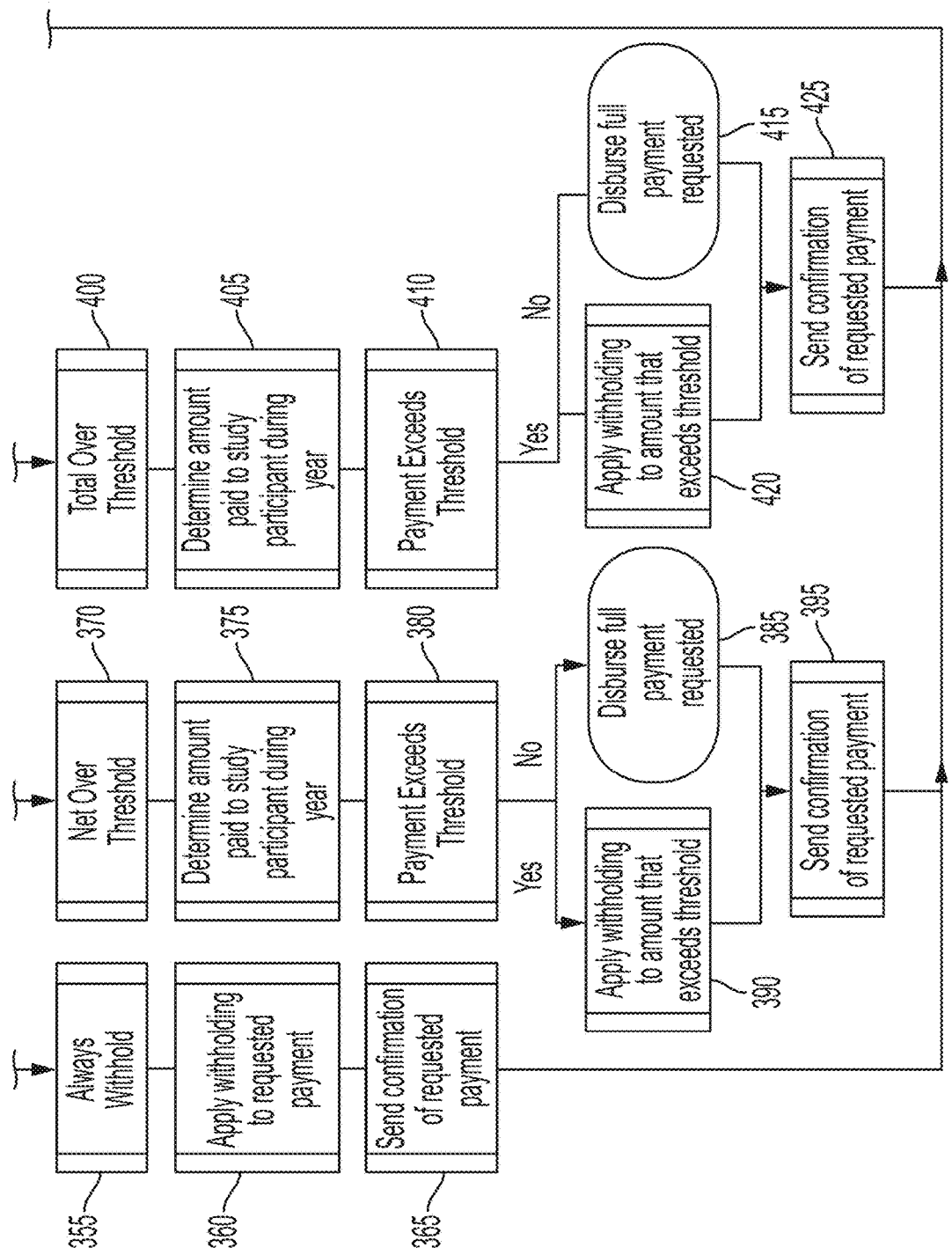
FIG. 7 shows an example GUI that displays a message when a valid TIN is not provided to the clinical management system.

FIG. 6 provides a flow chart 300 that illustrates exemplary operation of the Clinical Data Processing System 100, according to some embodiments. Starting at 305, information about the Study Participant is received, for example, following an initial registration of the Study Participant with the Clinical Data Processing System 100. This participant information may include personal information such as, for example, the Study Participant's address, home telephone number, etc. as well as the studies that he or she will be enrolled in. In some embodiments, the Study Participant's information is entered via a webpage interface with fields allowing entry of different types of information, e.g., via the computing devices 100a, 100b, under control of the User Interface Module 170. In other embodiments, information may be uploaded as a data file that is parsed by the Clinical Data Processing System to extract the relevant fields. For example, in one embodiment, the Investigator can upload a spreadsheet of participant information that is parsed to extract the relevant participant information. Note that, in this way, information for multiple participants can be uploaded to the Clinical Data Processing System simultaneously. Received participant information may be stored as Participant Data 200 in the Clinical Data Processing System 100.

Continuing with reference to FIG. 6, tax management settings are received at step 310. In some embodiments, these can be received with the other participant information at step 305; in other embodiments, the tax management settings are specified in a separate webpage or other interface (see, e.g., FIGS. 5A-5K). These settings may reflect a user/operator's preferences, e.g., based on the user/operator's interpretation of specific aspects of governing tax law, which may vary from user/operator to user/operator for the same governing tax law. The tax management settings may specify, for example, rules that for apply withholding purposes. By way of example, such settings may include options such as "Always Withhold," "Withhold for Total Over Threshold," "Withhold for Net Over Threshold," "Apply Hard Stop," and/or a "Withholding Percentage" to be applied. Such information may be received via the user interface windows displayed under control of the User Interface Module 170, in accordance with data received from the Schema Management Module 150 and/or Schema Data 190. Selected setting information may be stored as Participant Data 200 in the Clinical Data Processing System 100.

At step 315 payment instructions are received at the Clinical Data Processing System 100 from the investigators indicating an amount to pay the Study Participant for participation in one or more clinical studies. In accordance with the system's tax management functionality, it is next determined whether a valid TIN has been provided for a particular participant, as shown at 320. This may be determined by referencing the stored Participant Data, and/or by contacting an external validation system using the Validation Engine 180.

If it is determined at 320 that a valid TIN has been provided, then disbursement of the full requested payment may be performed or authorized, without the need for withholding, as shown at 325, and a confirmation of the approval or payment may be provided, as shown at 320, and flow returns to 315 to await a next payment instruction in this example.

If, however, it is determined at 320 that a valid TIN has not been provided, then the User Interface Module provides a notification to the user that the TIN is missing on invalid, as shown at 330. The User Interface Module 170 displays a prompt to enter a valid TIN and may gather such information, and it may be determined if a valid TIN has been provided, as shown at 320, e.g., by contacting an external validation system suing the Validation Engine. This may be performed by the Schema Management Module by referencing the stored Participant Data 200.

If a valid TIN is not provided, then it is determined whether a "Hard Stop" option has been selected for payment to the participant. If so, then the proposed payment is not approved or disbursed, but rather is held in a pending state, as shown at 335, and a confirmation of the requested payment is provided to the user as shown at 340 and flow returns to 315, as shown in FIG. 6. This may be performed by the Schema Management Module by referencing the stored Participant Data 200.

If a "Hard Stop" option has not been selected for payments to the participant, then it is determined which withholding approach has been selected for payments to the participant, as shown at 345 and 350. This may be performed by the Schema Management Module by referencing the stored Participant Data 200.

If it is determined that an "Always Withhold" tax management setting has been selected for payments to the participant (e.g., by the Schema Management Module by referencing the stored Participant Data 200) as shown at 355, then the system applies a withholding percentage (e.g., 28%) to the proposed payment, as shown at 360. This may involve mere determination of withholding and net payments amounts, e.g., by the Schema Management Module 150 with information received via the User Interface Module and/or data stored as Schema Data 190, or may further involve initiating the payment in embodiments in which the Clinical Data Processing System 100 includes payment functionality. If the Clinical Data Processing System is configured to make the payment then a payment amount is issued to the Study Participant (e.g., via a debit card account) equal to the amount requested by the investigators minus the withholding tax due. A confirmation of the payment is then sent to the site investigator as shown at 365. For example, this confirmation could take the form of a notification provided in the GUI, under the control of the User Interface Module 170, of the Clinical Data Processing System accessible to the Investigators. Alternatively (or additionally), an electronic message (e.g., e-mail, text message, etc.) could be sent to the investigators with the confirmation. As shown in FIG. 6, flow then returns to step 315.

If it is determined that a "Net Over Threshold" tax management setting has been selected for payments to the participant (e.g., by the Schema Management Module by referencing the stored Participant Data 200) as shown at 370, then the system determines an amount paid to the study participant during the relevant tax year, across all studies, as shown at 375. This determination may be performed by the Participation Aggregation Module, which aggregates data from multiple studies, by referencing the stored Participant Data 200. The system then determines if the proposed payment would make the total payments to the participant exceed an applicable threshold, as shown at 380. This may be performed by the Schema Management Module 150 with information stored as Schema Data 190 or Participant Data 200. If it is determined that the proposed payment would not make the total payments exceed the threshold, then the full proposed payment is approved, as shown at 385. If it is determined that the proposed payment would make the total payments exceed the threshold, then the net amount over the threshold is determined, and withholding is applied to the net amount, as shown at 390. For example, if the threshold is $600 and the participant has been paid $550 during the current year, a payment of $150 would place the participant $100 over the threshold, and withholding would be applied to the $100 net amount. This determination may be performed by the Schema Management Module 150 with information stored as Schema Data 190 or Participant Data 200. If the Clinical Data Processing System is configured to make the payment then a payment amount may be issued to the Study Participant (e.g., via a debit card account) equal to the amount requested by the investigators minus the withholding tax due. A confirmation of the payment is then sent to the site investigator as shown at 395. For example, this confirmation could take the form of a notification provided in the GUI, under the control of the User Interface Module 170, of the Clinical Data Processing System accessible to the Investigators. Alternatively (or additionally), an electronic message (e.g., e-mail, text message, etc.) could be sent to the investigators with the confirmation. As shown in FIG. 6, flow then returns to step 315.

If it is determined that a "Total Over Threshold" tax management setting has been selected for payments to the participant (e.g., by the Schema Management Module by referencing the stored Participant Data 200) as shown at 400, then the system determines an amount paid to the study participant during the relevant tax year, across all studies, as shown at 405. This determination may be performed by the Participation Aggregation Module, which aggregates data from multiple studies, by referencing the stored Participant Data 200. The system then determines if the proposed payment would make the total payments to the participant exceed an applicable threshold, as shown at 410. This may be performed by the Schema Management Module 150 with information stored as Schema Data 190 or Participant Data 200. If it is determined that the proposed payment would not make the total payments exceed the threshold, then the full proposed payment is approved, as shown at 415. If it is determined that the proposed payment would make the total payments exceed the threshold, then withholding is applied to the entire proposed payment amount that would make the total payments exceed the threshold, as shown at 420. For example, if the threshold is $600 and the participant has been paid $550 during the current year, a payment of $150 would place the participant $100 over the threshold, and withholding would be applied to the proposed $150 amount. This determination may be performed by the Schema Management Module 150 with information stored as Schema Data 190 or Participant Data 200. If the Clinical Data Processing System is configured to make the payment then a payment amount may be issued to the Study Participant (e.g., via a debit card account) equal to the amount requested by the investigators minus the withholding tax due. A confirmation of the payment is then sent to the site investigator as shown at 425. For example, this confirmation could take the form of a notification provided in the GUI, under the control of the User Interface Module 170, of the Clinical Data Processing System accessible to the Investigators. Alternatively (or additionally), an electronic message (e.g., e-mail, text message, etc.) could be sent to the investigators with the confirmation. As shown in FIG. 6, flow then returns to step 315.

Accordingly, the data processing may be performed in accordance with governing tax law, in a manner that is managed programmatically by the Clinical Data Processing System in accordance with applicable taxation-schema-specific rules stored in the memory of the system, and in a manner that accounts for user/operator preferences via user/operator-provided input as to how to comply with the taxation-schema on a user/operator-specific basis (e.g., to apply withholding to total or only to net amounts).

Figure 8:
FIG. 8 shows an example of a dashboard for managing study settings for a Study Participant, according to some embodiments.

FIG. 8 shows an example of a dashboard displayable by the User Interface Module 170 for managing study settings for a Study Participant, according to some embodiments. This dashboard illustrates how tax management for the Study Participant can be integrated with other information related to a study. Here, the study is named "Study XYZ." The top portion of the dashboard, labeled "Study Profile" includes general information about the study, including the Study Participant's status (enrolled or not enrolled), and their subject ID. In this case, the Study Participant is receiving payments via a debit card; thus, the "Study Profile" section includes card balance, card number, and the card's expiration date. The other information in the "Study Profile" section of the dashboard provides the Study Participant's address, time zone of their residence, their home phone number, and an indication of whether the Study Participant can be contacted via email.

Continuing with reference to FIG. 8, the dashboard includes a "Tax Management" section that lists the tax management settings for the Study Participant. In this example, TIN validation is enabled and the "Apply Withholding" option has been set (see FIG. 5F) and the withholding amount is set to be 28%. The withholding approach is "net over threshold," with a withholding threshold of $600.00 and a warning level of $400.00. The dashboard may be provided as a form of a report from the Participation Aggregation module 160, which may be displayed under the control of the User Interface Module 170.

The functions and process steps herein may be performed automatically, wholly or partially in response to user command. An activity (including a step) performed automatically is performed in response to one or more executable instructions or device operation without user direct initiation of the activity.

Additionally, computer readable media storing computer readable code executable by the processor to carry out the method steps identified above is provided. The computer readable media stores code for carrying out subprocesses for carrying out the methods described herein.

A computer program product recorded on a computer readable medium for carrying out the method steps identified herein is provided. The computer program product comprises computer readable code executable by the processor to carry out the methods described above.

While there have been described herein the principles of the invention, it is to be understood by those skilled in the art that this description is made only by way of example and not as a limitation to the scope of the invention. Accordingly, it is intended by the appended claims, to cover all modifications of the invention which fall within the true spirit and scope of the invention.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112(f), unless the element is expressly recited using the phrase "means for."

We claim:

1. A clinical data processing system comprising:
   a processor;
   a memory operatively coupled to the processor, the memory storing code comprising executable instructions that, when executed by the processor, causes the clinical data processing system to:
   provide, by display at a display device, a graphical user interface accessible at a clinical site, the graphical user interface enabling an investigator to enter via the graphical user interface respective participant information for each of a plurality of study participants, said respective participant information for each of the plurality of study participants comprising:
      (a) personal information corresponding to a respective study participant,
      (b) tax management settings comprising a withholding option specifying how withholding should be applied to clinical payments payable to the respective study participant, and
      (c) one or more requests for payment to the study participant for participation in one or more clinical studies, wherein each request comprises a payment amount corresponding to an activity related to a clinical study; and
   process each request for payment by:
      (i) automatedly referencing disparate tax schema rules, stored in memory, for determining at least one of taxation and withholding amounts according to a plurality of disparate tax schema for a plurality of tax jurisdictions, said plurality of tax jurisdictions comprising tax jurisdictions of multiple countries;
      (ii) automatedly identifying from among said disparate tax schema rules an applicable tax schema applicable to said study participant, based at least in part on said respective participant information for said respective study participant and said respective study participant's particular tax jurisdiction;
      (iii) automatedly determining a withholding amount to be applied to the payment amount of the request for the respective study participant based on the applicable tax schema and the tax management settings for the respective study participant;
      (iv) automatedly determining a reduced amount of payment due to the respective study participant by subtracting the withholding amount from the requested payment amount, according to the applicable tax schema and the tax management settings, for the respective study participant; and (v) automatedly transmitting a signal, via a communications network, to an external payment processing system, the transmitted signal controlling the external payment processing system to cause it to electronically issue a payment to the respective study participant in the determined reduced amount of payment due.

2. The clinical data processing system of claim 1, wherein the memory stores code comprising executable instructions that, when executed by the processor, causes the clinical data processing system to:

generate an unblinded withholding report comprising:
personal information corresponding to the study participant,
a description of each payment to the debit card account, and
a total withholding amount equal to the summation of the withholding amount from each request for payment; and
transmit the unblinded report to the clinical study.

3. The clinical data processing system of claim 1, wherein the memory stores code comprising executable instructions that, when executed by the processor, causes the clinical data processing system to:

generate a de-identified subject identifier for the study participant;
generate a blinded withholding report comprising:
the de-identified subject identifier,
a description of each payment to the debit card account, and
a total withholding amount equal to the summation of the withholding amount from each request for payment, and
transmit the blinded withholding report to one or more sponsors of the clinical study.

4. The clinical data processing system of claim 1, wherein the tax management settings comprise a withholding percentage and the withholding amount applied for each request for payment is equal to the product of the withholding percentage and the requested payment amount.

5. The clinical data processing system of claim 1, wherein the withholding option specifies that withholding is applied to all payments to the study participant for participation in clinical studies.

6. The clinical data processing system of claim 1, wherein the withholding option specifies that withholding is only applied after the study participant's year-to-date earnings for participation in the clinical studies exceed a predetermined monetary threshold specified in the tax management settings.

7. The clinical data processing system of claim 1, wherein (a) the withholding option specifies that withholding is only applied to payments to the study participant above a monetary threshold in a single year and (b) the monetary threshold is specified in the tax management settings.

8. The clinical data processing system of claim 1, wherein the memory stores code comprising executable instructions that, when executed by the processor, causes the clinical data processing system to:

determine whether the tax management settings include a tax identification number (TIN) for the study participant; and
if the tax management settings do not include the TIN for the study participant, (a) provide a notification in the graphical user interface that payments are subject to default withholding rules until the TIN is provided, and
(b) determine withholding amount to be applied to the payment amount of the request based on the default withholding rules.

9. A computer-implemented method for performing data processing for clinical trial administration, the method comprising the following implemented by a computerized clinical data processing system comprising at least one processor and a memory operatively coupled to the processor and storing instructions executable by the processor:

providing, by displaying at a display device, a graphical user interface accessible at a clinical site, the graphical user interface enabling an investigator to enter respective participant information for each of a plurality of study participants, said respective participant information for each of the plurality of study participants comprising:
(a) personal information corresponding to a respective study participant,
(b) tax management settings comprising a withholding option specifying how withholding should be applied to clinical payments to the respective study participant, and
(c) one or more requests for payment to the respective study participant for participation in one or more clinical studies, wherein each request comprises a payment amount corresponding to an activity related to a clinical study; and
processing each request for payment by:
(i) automatedly referencing disparate tax schema rules, stored in memory, for determining at least one of taxation and withholding amounts according to a plurality of disparate tax schema for a plurality of tax jurisdictions, said plurality of tax jurisdictions comprising tax jurisdictions of multiple countries;
(ii) automatedly identifying from among said disparate tax schema rules an applicable tax schema applicable to said study participant, based at least in part on said respective participant information for said respective study participant and said respective study participant's particular tax jurisdiction;
(iii) automatedly determining a withholding amount to be applied to the payment amount of the request for the respective study participant based on the applicable tax schema and the tax management settings for the respective study participant;
(iv) automatedly determining a reduced amount of payment due to the study participant by subtracting the withholding amount from the requested payment amount, according to the applicable tax schema and the tax management settings, for the respective study participant; and
(v) automatedly transmitting a signal, via a communications network, to an external payment processing system, the transmitted signal controlling the external payment processing system to cause it to electronically issue a payment to the respective study participant in the determined reduced amount of payment due.

10. The method of claim 9, further comprising:
generating an unblinded withholding report comprising:
personal information corresponding to the study participant,
a description of each payment to the debit card account, and a total withholding amount equal to the summation of the withholding amount from each request for payment; and transmitting the unblinded report to the clinical study.

11. The method of claim 9, further comprising:

generating a de-identified subject identifier for the study participant;

generating a blinded withholding report comprising:

the de-identified subject identifier, a description of each payment to the debit card account, and a total withholding amount equal to the summation of the withholding amount from each request for payment, and transmitting the blinded withholding report to one or more sponsors of the clinical study.

12. The method of claim 9, wherein the tax management settings comprise a withholding percentage and the withholding amount applied for each request for payment is equal to the product of the withholding percentage and the requested payment amount.

13. The method of claim 9, wherein the withholding option specifies that withholding is applied to all payments to the study participant for participation in clinical studies.

14. The method of claim 9, wherein the withholding option specifies that withholding is only applied after the study participant's year-to-date earnings for participation in the clinical studies exceed a predetermined monetary threshold specified in the tax management settings.

15. The method of claim 9, wherein (a) the withholding option specifies that withholding is only applied to payments to the study participant above a monetary threshold in a single year and (b) the monetary threshold is specified in the tax management settings.

16. The method of claim 9, further comprising:

determining whether the tax management settings include a tax identification number (TIN) for the study participant; and if the tax management settings do not include the TIN for the study participant, (a) providing a notification in the graphical user interface that payments are subject to default withholding rules until the TIN is provided, and (b) determining withholding amount to be applied to the payment amount of the request based on the default withholding rules.

17. A computer program product for performing data processing for clinical trial administration, the computer program product comprising a non-transitory computer-readable medium storing executable instructions that, when executed by a processor, cause a computerized clinical data processing system to perform a method comprising:

providing, by displaying via a display device, a graphical user interface accessible at a clinical site, the graphical user interface enabling an investigator to enter respective participant information for each of a plurality of study participants, said respective participant information for each of the plurality of study participants comprising:

(a) personal information corresponding to a respective study participant, (b) tax management settings comprising a withholding option specifying how withholding should be applied to clinical payments to the respective study participant, and (c) one or more requests for payment to the respective study participant for participation in one or more clinical studies, wherein each request comprises a payment amount corresponding to an activity related to a clinical study; and processing each request for payment by:

(i) automatedly referencing disparate tax schema rules, stored in memory, for determining at least one of taxation and withholding amounts according to a plurality of disparate tax schema for a plurality of tax jurisdictions, said plurality of tax jurisdictions comprising tax jurisdictions of multiple countries;

(ii) automatedly identifying from among said disparate tax schema rules an applicable tax schema applicable to said study participant, based at least in part on said respective participant information for said respective study participant and said respective study participant's particular tax jurisdiction;

(iii) automatedly determining a withholding amount to be applied to the payment amount of the request for the respective study participant based on the applicable tax schema and the tax management settings for the respective study participant;

(iv) automatedly determining an amount of payment due to the respective study participant by subtracting the withholding amount from the requested payment amount, according to the applicable tax schema and the tax management settings, for the respective study participant; and (v) automatedly transmitting a signal, via a communications network, to an external payment processing system, the transmitted signal controlling the external payment processing system to cause it to electronically issue a payment to the respective study participant in the determined reduced amount of payment due.

* * * * *